(12) United States Patent
Hamada et al.

(10) Patent No.: US 11,925,507 B2
(45) Date of Patent: Mar. 12, 2024

(54) ACOUSTIC MATCHING SHEET, COMPOSITION FOR ACOUSTIC MATCHING LAYER, ACOUSTIC WAVE PROBE, ACOUSTIC WAVE MEASUREMENT APPARATUS, AND METHOD FOR MANUFACTURING ACOUSTIC WAVE PROBE

(71) Applicant: FUJIFILM Corporation, Tokyo (JP)

(72) Inventors: Kazuhiro Hamada, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 354 days.

(21) Appl. No.: 17/484,684

(22) Filed: Sep. 24, 2021

(65) Prior Publication Data

US 2022/0008037 A1   Jan. 13, 2022

Related U.S. Application Data

(63) Continuation of application No. PCT/JP2020/012479, filed on Mar. 19, 2020.

(30) Foreign Application Priority Data

Mar. 29, 2019   (JP) ................................ 2019-068736

(51) Int. Cl.
*A61B 8/00* (2006.01)

(52) U.S. Cl.
CPC .......... *A61B 8/4281* (2013.01); *A61B 8/4444* (2013.01)

(58) Field of Classification Search
CPC ................................................... A61B 8/4281
See application file for complete search history.

(56) References Cited

U.S. PATENT DOCUMENTS

| 8,292,818 | B2* | 10/2012 | Yamashita | ........... A61B 8/4281 |
| | | | | 600/459 |
| 10,610,199 | B2* | 4/2020 | Morita | .................. A61B 8/4444 |
| 2005/0070801 | A1* | 3/2005 | Yamashita | ........... A61B 8/4281 |
| | | | | 600/459 |

(Continued)

FOREIGN PATENT DOCUMENTS

| CN | 1626041 A | 6/2005 |
| CN | 101081169 A | 12/2007 |

(Continued)

OTHER PUBLICATIONS

Extended European Search Report dated Apr. 4, 2022 in corresponding Application No. 20784651.0.

(Continued)

*Primary Examiner* — Colin T. Sakamoto
(74) *Attorney, Agent, or Firm* — Sughrue Mion, PLLC

(57) ABSTRACT

Provided are an acoustic matching sheet containing the following component (B) in the following component (A), a composition for an acoustic matching layer, an acoustic wave probe, an acoustic wave measurement apparatus, and a method for manufacturing an acoustic wave probe. (A) is at least one of a resin or a rubber; and (B) is at least one of a resin particle or a rubber particle having an acoustic velocity lower than an acoustic velocity of the component (A) and having a number average particle diameter of 1.0 μm or less.

17 Claims, 1 Drawing Sheet

(56) References Cited

U.S. PATENT DOCUMENTS

| | | | |
|---|---|---|---|
| 2007/0161903 A1* | 7/2007 | Yamashita | A61B 8/14 600/459 |
| 2007/0205697 A1 | 9/2007 | Chaggares et al. | |
| 2007/0282204 A1* | 12/2007 | Yamashita | G10K 11/02 600/459 |
| 2009/0069486 A1* | 3/2009 | Yamashita | A61B 8/4281 524/440 |
| 2013/0221805 A1 | 8/2013 | Ogura et al. | |
| 2014/0249419 A1 | 9/2014 | Morita | |
| 2016/0338666 A1* | 11/2016 | Morita | A61B 8/4444 |

FOREIGN PATENT DOCUMENTS

| | | |
|---|---|---|
| CN | 101172044 A | 5/2008 |
| CN | 102959993 A | 3/2013 |
| CN | 103458796 A | 12/2013 |
| JP | 62-11897 A | 1/1987 |
| JP | 2002-58099 A | 2/2002 |
| JP | 2008-11494 A | 1/2008 |
| JP | 2011-77572 A | 4/2011 |
| JP | 2014-168489 A | 9/2014 |

OTHER PUBLICATIONS

International Search Report dated May 26, 2020 from the International Searching Authority in International Application No. PCT/JP2020/012479.

Written Opinion dated May 26, 2020 from the International Bureau in International Application No. PCT/JP2020/012479.

International Preliminary Report on Patentability dated Sep. 28, 2021 with translation of the Written Opinion from the International Bureau in International Application No. PCT/JP2020/012479.

Chinese Office Action dated Sep. 5, 2023 in Application No. 202080025275.4.

* cited by examiner

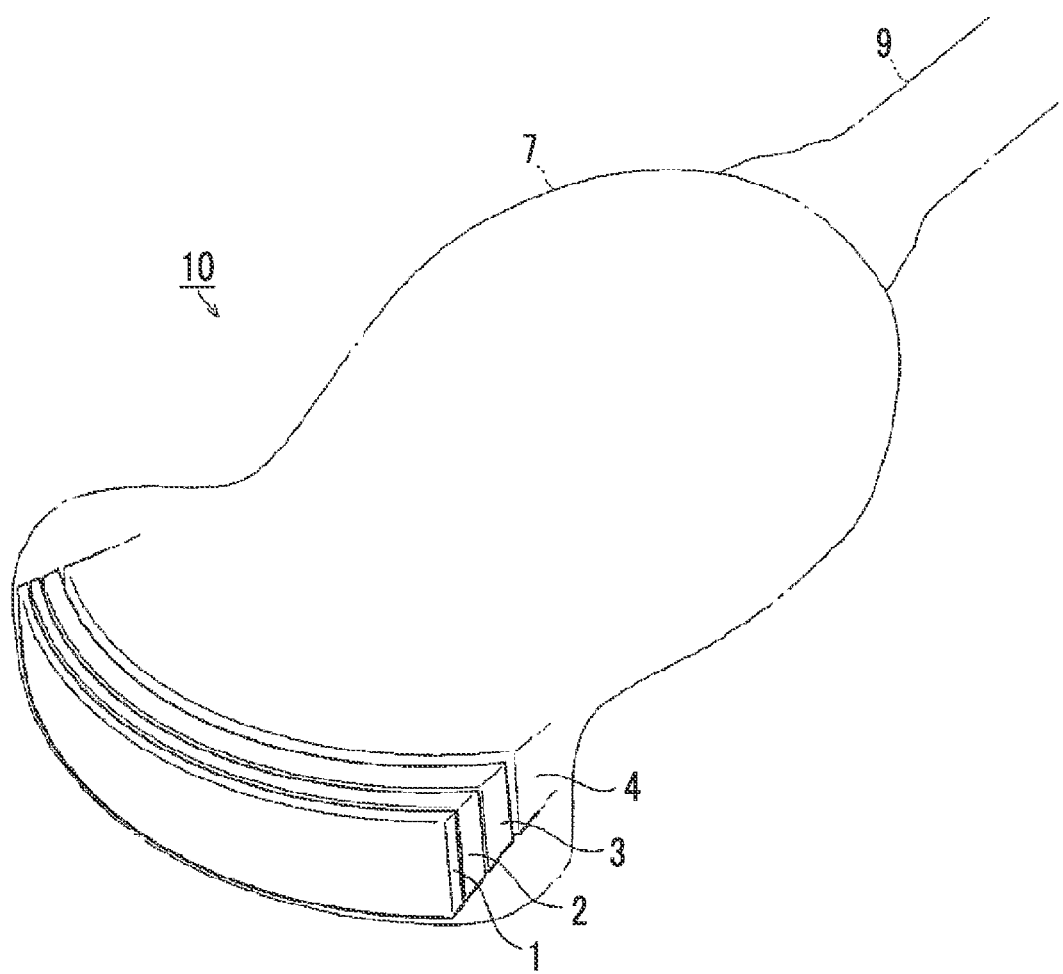

ACOUSTIC MATCHING SHEET, COMPOSITION FOR ACOUSTIC MATCHING LAYER, ACOUSTIC WAVE PROBE, ACOUSTIC WAVE MEASUREMENT APPARATUS, AND METHOD FOR MANUFACTURING ACOUSTIC WAVE PROBE

CROSS-REFERENCE TO RELATED APPLICATIONS

This application is a Continuation of PCI international Application No. PCT/JP2020/012479 filed on Mar. 19, 2020, which claims priority under 35 U.S.C. § 119 (a) to Japanese Patent Application No. 2019-068736 filed in Japan on Mar. 29, 2019. Each of the above applications is hereby expressly incorporated by reference, in its entirety, into the present application.

BACKGROUND OF THE INVENTION

1. Field of the Invention

The present invention relates to an acoustic matching sheet, a composition for an acoustic matching layer, an acoustic wave probe, an acoustic wave measurement apparatus, and a method for manufacturing an acoustic wave probe.

2. Description of the Related Art

In an acoustic wave measurement apparatus, an acoustic wave probe is used which irradiates a test object such as a living body with an acoustic wave, receives a reflected wave (echo) therefrom, and outputs a signal. The reflected wave received by this acoustic wave probe is converted into an electric signal which is then displayed as an image. Accordingly, the interior of the test object can be visualized and observed by using the acoustic wave probe.

As the acoustic wave, an ultrasonic wave, a photoacoustic wave, or the like is appropriately selected according to the test object and the measurement conditions.

For example, an ultrasound diagnostic apparatus, which is a kind of acoustic wave measurement apparatus, transmits an ultrasonic wave to the interior of a test object, receives the ultrasonic wave reflected by the tissues inside the test object, and displays the received ultrasonic wave as an image.

In addition, a photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave to generate heat in a case where the test object is irradiated with an electromagnetic wave pulse of visible light, near infrared light, microwave, or the like.

Since the acoustic wave measurement apparatus transmits and receives an acoustic wave to and from a test object, the acoustic wave probe is required to match the acoustic impedance with the test object (typically a human body). To satisfy this requirement, the acoustic wave probe is provided with an acoustic matching layer. This will be described by taking, as an example, a probe for an ultrasound diagnostic apparatus (also referred to as an ultrasound probe), which is a kind of acoustic wave probe.

The ultrasound probe includes a piezoelectric element that transmits and receives an ultrasonic wave and an acoustic lens that comes into contact with a living body, in which an acoustic matching layer is arranged between the piezoelectric element and the acoustic lens. An ultrasonic wave oscillated from the piezoelectric element is incident on a living body after being transmitted through the acoustic matching layer, further being transmitted through the acoustic lens. There is usually a difference in acoustic impedance (density×acoustic velocity) between the acoustic lens and the living body. In a case where this difference is large, the ultrasonic wave is easily reflected on the surface of the living body, and the incident efficiency of the ultrasonic wave into the living body is lowered. Therefore, the acoustic lens is required to have an acoustic impedance characteristic close to that of the living body.

On the other hand, the difference in acoustic impedance between the piezoelectric element and the living body is generally large. Accordingly, the difference in acoustic impedance between the piezoelectric element and the acoustic lens is also usually large. Therefore, in a case of a laminated structure of the piezoelectric element and the acoustic lens, the ultrasonic wave emitted from the piezoelectric element is reflected on the surface of the acoustic lens, and therefore the incident efficiency of the ultrasonic wave on the living body is lowered. In order to suppress this reflection of the ultrasonic wave, the above-mentioned acoustic matching layer is provided between the piezoelectric element and the acoustic lens. The acoustic impedance of the acoustic matching layer takes a value between the acoustic impedance of the living body or the acoustic lens and the acoustic impedance of the piezoelectric element, which leads to improved propagation efficiency of an ultrasonic wave from the piezoelectric element to the living body. In addition, in recent years, the development of an acoustic matching layer with more efficient propagation of an ultrasonic wave has been underway by providing a gradient in acoustic impedance from the piezoelectric element side to the acoustic lens side, through a configuration of an acoustic matching layer having a multi-layer structure in which a plurality of acoustic matching sheets (acoustic matching layer materials) are laminated.

It is known that a thermosetting resin, silicone resin particles, and the like are used as the material of the acoustic matching sheet constituting the acoustic matching layer having a multi-layer structure (for example, JP2014-168489A).

SUMMARY OF THE INVENTION

The gradient of the acoustic impedance in the above-mentioned acoustic matching layer is designed such that the closer to the piezoelectric element, the larger the acoustic impedance of the acoustic matching sheet, and the closer to the acoustic lens, the smaller the acoustic impedance of the acoustic matching sheet. That is, an acoustic matching sheet having acoustic impedance close to that of the piezoelectric element (usually about $25 \times 10^6$ kg/m$^2$/sec) is required on the piezoelectric element side; and an acoustic matching sheet having acoustic impedance close to that of the living body (1.4 to $1.7 \times 10^6$ kg/m$^2$/sec in the human body) is required on the acoustic lens side. From the viewpoint of making the gradient of the acoustic impedance gentler, it is required to increase the number of laminated acoustic matching sheets having different acoustic impedances.

The acoustic impedance of the acoustic matching sheet can be adjusted by the density and acoustic velocity of the sheet constituent material. In order to provide a desired gradient in acoustic impedance by forming the acoustic matching layer into a multi-layer structure, it is also necessary to prepare an acoustic matching sheet in which the acoustic velocity is suppressed.

In addition, the acoustic matching layer having a multi-layer structure is usually produced by laminating acoustic matching sheets and heating the laminated sheets, That is, the acoustic matching sheet is required to have heat resistance since molten solder or the like is used to fix the electrodes to the acoustic matching layer. Further, the acoustic matching sheet is required to have a sufficient ultrasonic wave (acoustic wave) sensitivity in order to transmit and receive an ultrasonic wave (acoustic wave) with high sensitivity.

However, as a result of studies by the present inventors, it has been found for the acoustic matching sheet constituting the acoustic matching layer described in JP2014-168489A that it is difficult to raise both the heat resistance and the acoustic wave sensitivity to a desired level while achieving a low acoustic velocity.

An object of the present invention is to provide an acoustic matching sheet having a low acoustic velocity, a sufficient heat resistance, and a sufficient acoustic wave sensitivity, and a composition for an acoustic matching layer which is suitable for forming the acoustic matching sheet.

Another object of the present invention is to provide an acoustic wave probe having the acoustic matching sheet of the present invention as an acoustic matching layer, and an acoustic wave measurement apparatus using the acoustic wave probe.

Another object of the present invention is to provide a method for manufacturing an acoustic wave probe, including a step of forming an acoustic matching layer using a composition for forming the acoustic matching sheet of the present invention.

As a result of extensive studies in view of the foregoing objects, the present inventors have found that a sheet, which is made by using at least one of a resin or a rubber as a base material and including, in this base material, at least one of a resin particle or a rubber particle having an acoustic velocity lower than that of the base material and a number average particle diameter of a specific value or less, is capable of reducing the acoustic velocity of the sheet while suppressing a decrease in heat resistance and acoustic wave sensitivity due to the inclusion of the above particles. Based on this finding, the present invention has been further studied and completed.

That is, the foregoing objects of the present invention have been achieved by the following configurations.

<1>
An acoustic matching sheet comprising the following component (B) in the following component (A):
(A): at least one of a resin or a libber, and
(B): at least one of a resin particle or a rubber particle having an acoustic velocity lower than an acoustic velocity of the component (A) and having a number average particle diameter of 1.0 µm or less.

<2>
The acoustic matching sheet according to <1>, in which the number average panicle diameter of the component (B) is 0.5 µm or less.

<3>
The acoustic matching sheet according to <2>, in which the number average particle diameter of the component (B) is 0.2 µm or less.

<4>
The acoustic matching sheet according to any one of <1> to <3>, in which the component (A) is at least one of an epoxy resin or a polyamide resin.

<5>
The acoustic matching sheet according to <4>, in which the component (A) is an epoxy resin.

<6>
The acoustic matching sheet according to <5>, in which the component (A) is at least one of a bisphenol A type epoxy resin, a bisphenol F type epoxy resin, or a phenol novolac type epoxy resin.

<7>
The acoustic matching sheet according to any one of <1> to <6>, in which the component (B) is at least one of an acrylic resin particle, a silicone resin particle, or a rubber particle.

<8>
The acoustic matching sheet according to <7>, in which the component (B) is at least one of a silicone resin particle or a rubber particle.

<9>
The acoustic matching sheet according to <8>, in which the component (B) is a rubber particle.

<10>
The acoustic matching sheet according to any one of <1> to <9>, further comprising (C): a metal particle.

<11>
The acoustic matching sheet according to <10>, in which a metal element constituting the component (C) includes at least one of metal elements of Groups 4 to 13.

<12>
The acoustic matching sheet according to <11>, in which the metal element constituting the component (C) includes at least one of Zn, In, Au, Ag, Co, Zr, Ta, Fe, Cu, Ni, Nb, Pt, Mn, or Mo.

A composition for an acoustic matching layer, comprising components (A1) and (B1):
(A1): at least one of a resin or a rubber, and
(B1): at least one of a resin particle or a rubber particle having an acoustic velocity lower than an acoustic velocity of the component (A1) and having a number average particle diameter of 1.0 µm or less.

<14>
An acoustic wave probe comprising the acoustic matching sheet according to any one of <1> to <12> in an acoustic matching layer.

<15>
An acoustic wave measurement apparatus comprising the acoustic wave probe according to <14>.

<16>
The acoustic wave measurement apparatus according, to <15>, in which the acoustic wave measurement apparatus is an ultrasound diagnostic apparatus.

<17>
A method for manufacturing an acoustic wave probe, comprising a step of forming an acoustic matching layer using the composition for an acoustic matching layer according to <13>.

In the description of the present invention, the expression "to" is used to mean that numerical values described before and after "to" are included as a lower limit value and an upper limit value, respectively.

In the description of the present invention, in a case where the number of carbon atoms in a certain group is specified, the number of carbon atoms means the number of carbon atoms in the entire group. That is, in a case where this group is in a form further having a substituent, the number of carbon atoms means the number of carbon atoms in the entire group including this substituent.

In the description of the present invention, in a case where there are a plurality of substituents, linking groups, or the like (hereinafter, referred to as substituents or the like) represented by specific reference numerals, or in a case where a plurality of substituents or the like are simultaneously or selectively specified, it means that the substituents or the like may be the same as or different from each other. In addition, even in a case of being not particularly specified, it means that, in a case where a plurality of substituents or the like are adjacent to each other, the plurality of substituents or the like may be linked or fused to each other to form a ring.

An acoustic matching sheet according to an aspect of the present invention has a low acoustic velocity, a sufficient heat resistance, and a sufficient acoustic wave sensitivity.

In addition, a composition for an acoustic matching layer according to the aspect of the present invention is capable of providing an acoustic matching sheet having a low acoustic velocity, a sufficient heat resistance, and a sufficient acoustic wave sensitivity by forming or processing the composition into a desired sheet.

In addition, an acoustic wave probe according to the aspect of the present invention, and an acoustic wave measurement apparatus according to the aspect of the present invention using the acoustic wave probe have a sufficient acoustic wave sensitivity.

In addition, according to a method for manufacturing an acoustic wave probe according to the aspect of the present invention, the acoustic wave probe according to the aspect of the present invention can be obtained by using a composition for forming the acoustic matching sheet according to the aspect of the present invention.

BRIEF DESCRIPTION OF DRAWINGS

The FIGURE is a perspective view of an example of a convex ultrasound probe which is an aspect of an acoustic wave probe.

DESCRIPTION OF THE PREFERRED EMBODIMENTS

[Acoustic Matching Sheet]

The acoustic matching sheet according to the embodiment of the present invention (hereinafter, also simply referred to as "the sheet according to the embodiment of the present invention") contains the following component (B) in the following component (A).

(A): at least one of a resin or a rubber.

(B): at least one of a resin particle or a rubber particle having an acoustic velocity lower than an acoustic velocity of the component (A) and having a number average particle diameter of 1.0 µm or less.

In the sheet according to the embodiment of the present invention, it is preferable that the component (A) is used as a matrix, the component (B) is dispersed in the matrix, and the component (B) is uniformly dispersed.

A gradient of the acoustic impedance may be seen in the sheet according to the embodiment of the present invention. For example, in a case where the gradient of the acoustic impedance is seen along any one direction of the sheet, there may be a gradient in the dispersibility (abundance ratio) of the component (B) along the above direction.

The reason why the sheet according to the embodiment of the present invention has a low acoustic velocity, an excellent heat resistance, and further an excellent acoustic wave sensitivity due to having the above-mentioned configuration is not clear, but it is presumed as follows.

In the component (A) as a matrix, particles of the component (B) having an acoustic velocity lower than that of the matrix, that is, having a volume elastic modulus lower than that of the matrix are dispersed. It is considered that, since the component (B) is a particle, a crosslink density of the component (A) is not affected even in a case where the component (A) is crosslinked (cured); accordingly, the acoustic velocity can be reduced while suppressing a decrease in heat resistance exhibited by the matrix itself. Further, it is considered that, in a case where the number average particle diameter of the particles is 1.0 µm or less, a decrease in the attenuation of the acoustic wave is suppressed, and therefore the acoustic wave sensitivity of the acoustic matching sheet can be improved in addition to suppressing a decrease in heat resistance and reducing the acoustic velocity as described above.

<Component (A)>

The sheet according to the embodiment of the present invention contains at least one of a resin or a rubber as the component (A). Examples of the resin include a thermosetting resin and a thermoplastic resin.

The component (A) is preferably at least one of a thermosetting resin or a thermoplastic resin from the viewpoint of acoustic velocity control, and more preferably a thermosetting resin from the viewpoint of acoustic velocity control range.

The thermosetting resin used in the present invention is not particularly limited, and examples thereof include an epoxy resin, a urethane resin, a silicone resin, a phenol resin, a urea resin, and a melamine resin, among which an epoxy resin, a urethane resin, a silicone resin, and a phenol resin are preferable, and an epoxy resin is more preferable.

The epoxy resin used in the present invention includes at least one epoxy resin of a bisphenol A type epoxy resin, a bisphenol F type epoxy resin, or a phenol novolac type epoxy resin.

The bisphenol A type epoxy resin used in the present invention is not particularly limited, and any bisphenol A type epoxy resin commonly used as a main agent of an epoxy-based adhesive can be widely used. Preferred specific examples of the bisphenol A epoxy resin include bisphenol A diglycidyl ethers (jER825, jER828, and jER834 (all trade names), manufactured by Mitsubishi Chemical Corporation) and bisphenol A propoxylate diglycidyl ethers (manufactured by Sigma-Aldrich Co. LLC).

The bisphenol F type epoxy resin used in the present invention is not particularly limited, and any bisphenol. F type epoxy resin commonly used as a main agent of an epoxy-based adhesive can be widely used. Preferred specific examples of the bisphenol F type epoxy resin include bisphenol F diglycidyl ether (trade name: EPICLON 830, manufactured by DIC Corporation) and 4,4'-methylenebis (N,N-dialycidylaniline).

The phenol novolac type epoxy resin used in the present invention is not particularly limited, and any phenol novolac type epoxy resin commonly used as a main agent of an epoxy-based adhesive can be widely used. Such a phenol novolac type epoxy resin is commercially available, for example, under the product number 406775 from Sigma-Aldrich Co. LLC.

The epoxy resin may consist of the above-mentioned epoxy resins or may include, in addition to the above-mentioned epoxy resins, another epoxy resin (for example, an aliphatic epoxy resin) as long as the effects of the present invention are not impaired. The content of the above three types of epoxy resins (total content of a bisphenol A type epoxy resin, a bisphenol F type epoxy resin, and a phenol novolac type epoxy resin) in the epoxy resin is preferably 80% by mass or more and more preferably 90% by mass or more.

In the sheet according to the embodiment of the present invention, the thermosetting resin out of the component (A) is heated in the sheet manufacturing process and cured in the sheet. In a case where the thermosetting resin is cured by reacting with a curing agent which will be described later, the thermosetting resin may be in a cured state by reacting with this curing agent. The same applies to a thermosetting component other than the thermosetting resin out of the component (A). In addition, the rubber out of the component (A) may be a crosslinked substance.

That is, the component (A) specified in the sheet according to the embodiment of the present invention includes a cured substance of the component (A), a compound in which the component (A) is cured by a curing agent, and a crosslinked substance of the components (A). In addition, the component (A) may be bonded to the surface of the component (B).

Examples of the urethane resin include TAKELAC and TAKENATE (both trade names, manufactured by Mitsui Chemicals, Inc.) and PANDEX (trade name, manufactured by DIC Corporation).

Examples of the silicone resin include KR220 and KR300 (both trade names, manufactured by Shin-Etsu Silicone Co., Ltd.) and ELASTOSIL (trade name, manufactured by Wacker Asahikasei Silicone Co., Ltd.).

Examples of the phenol resin include J-325, 5010, and 5592 (all trade names, manufactured by DIC Corporation).

Examples of the urea resin include AMIDIR G-1850 and AMIDIR P-138 (both trade names, manufactured by DIC Corporation), and FLEAMIN M (trade name, manufactured by Daiwa Co., Ltd.).

Examples of the melamine resin include AMIDIR L-105-60 (trade name, manufactured by DIC Corporation) and FLEAMIN Z (trade name, manufactured by Daiwa Co., Ltd.).

The thermoplastic resin used in the present invention is not particularly limited, and examples thereof include a polyamide resin, an acrylic resin, a polyethylene resin, a polypropylene resin, a polyamideimide resin, and a polyetheretherketone resin, among which a polyamide resin, an acrylic resin, and a polypropylene resin are preferable, and a polyamide resin is more preferable.

Examples of the polyamide resin used in the present invention include nylon 6, nylon 66, nylon 46, nylon 610, nylon 11, nylon 12, nylon 6T, and nylon 9T.

Examples of the acrylic resin include DELPET (trade name, manufactured by Asahi Kasei Corporation), ALTUGLAS (trade name, manufactured by Arkema S. A.), and ACRYPET (trade name, manufactured by Mitsubishi Chemical Corporation).

Examples of the polyethylene resin include SUNTEC, CREOLEX, and SUNFINE (all trade names, manufactured by Asahi Kasei Corporation).

Examples of the polypropylene resin include SUMISTRAN and SUMITOMO NOBLEN (both trade names, manufactured by Sumitomo Chemical Co., Ltd.), and DAICEL PP (trade name, manufactured by Daicel Miraizu Ltd.).

Examples of the polyamideimide resin include TORLON polyamideimide (trade name, manufactured by Solvay Specialty Polymers Japan K.K.).

Examples of the polyetheretherketone resin include VICTREX PEEK (trade name, manufactured by Victrex Japan Inc.) and VESTAKEEP (trade name, manufactured by Daicel-Evonik Ltd.).

The rubber used in the present invention is not particularly limited, and examples thereof include a polyisoprene rubber, a polybutadiene rubber, an ethylene propylene diene (EPDM) rubber, a styrene, butadiene rubber, an ethylene propylene rubber, and a butyl rubber, among which a polyisoprene rubber, a polybutadiene rubber, and an ethylene propylene diene rubber are preferable.

The component (A) may be used alone or in combination of two or more thereof.

<Component (B)>

The sheet according to the embodiment of the present invention includes at least one of a thermosetting resin particle, a thermoplastic resin particle, or a rubber particle, each having an acoustic velocity lower than that of the component (A) and having a number average particle diameter of 1.0 µm or less, as the component (B).

The acoustic velocity of the component (B) may be lower than that of the component (A), and the difference between the acoustic velocity of the component (A) and the acoustic velocity of the component (B) ("acoustic velocity of component (A)"—"acoustic velocity of component (B)") is preferably 50 to 1500 m/s, more preferably 100 to 1000 m/s, and still more preferably 400 to 1000 m's.

The component (B) is preferably at least one of a thermosetting resin particle or a rubber particle from the viewpoint of acoustic velocity control, and more preferably a rubber particle from the viewpoint of acoustic velocity control range.

The acoustic velocity of the component (B) used in the present invention is lower than the acoustic velocity of the component (A). The acoustic velocity of component (A) and component (B) is measured by the method described in Examples which will be given later. The acoustic velocity of the component (A) in a case where the component (A) is cured by the curing agent which will be described later refers to an acoustic velocity of the cured component (A). The same applies to the component (B).

The number average particle diameter of the component (B) used in the present invention is 1.0 µm or less. The number average particle diameter is preferably 0.5 µm or less and more preferably 0.2 µm or less, from the viewpoint of further improving the acoustic wave sensitivity. The lower limit of the number average particle diameter is not particularly limited, but it is practically 0.01 µm or more.

The number average particle diameter is a value measured by the method described in Examples which will be given later.

The thermosetting resin particle used in the present invention is not particularly limited as long as it is a thermosetting resin particle, and examples thereof include a silicone resin particle, a polyurethane resin particle, an epoxy resin particle, and an unsaturated polyester resin particle, among which a silicone resin particle and a polyurethane resin particle are preferable, and a silicone resin particle is more preferable.

Examples of the silicone resin particle include TOSPEARL (trade name, manufactured by Momentive Performance Materials Japan LLC).

The thermoplastic resin particle used in the present invention is not particularly limited as long as it is a thermoplastic resin particle, and examples thereof include an acrylic resin particle, a polyethylene resin particle, a polypropylene resin particle, an ABS resin particle, and a polyethylene terephthalate resin particle, among which an acrylic resin particle, a polyethylene resin particle, and a polypropylene resin particle are preferable, and an acrylic resin particle is more preferable.

Examples of the acrylic resin particle include EPOSTAR (trade name, manufactured by Nippon Shokubai Co., Ltd.).

Examples of the rubber particle used in the present invention include the rubber particles described in the component (A), among which at least one of a polyisoprene rubber particle or a polybutadiene rubber particle is preferable.

The component (B) may be used alone or in combination of two or more thereof.

Among the thermosetting resin particles, those having a number average particle diameter of larger than 1.0 μm can be used by reducing the number average particle diameter to 1.0 μm or less by wet pulverization or the like.

The component (B) may be used alone or in combination of two or more thereof.

Products containing the components (A) and (B), such as KANE ACE (registered trademark, grades: MX-153, MX-257, MX-154, MX-960, MX-136, MX-965, MX-214, MX-227M75, MX-334M75, MX-416, and MX-451, manufactured by Kaneka Corporation) and ACRYSET (registered trademark, grades: BPA328 and BPA307, manufactured by Nippon Shokubai Co., Ltd.), can also be used.

<Component (C)>

The sheet according to the embodiment of the present invention may contain a metal particle as the component (C). By including the metal particle in the sheet, the density of the sheet can be increased while satisfying the desired acoustic velocity, heat resistance, and acoustic wave sensitivity. In addition, by adjusting the content of the metal particle in the sheet, the density of the sheet can be easily adjusted, and the acoustic impedance of the obtained acoustic matching layer can be adjusted to a desired level. The metal particle may be surface-treated.

The surface treatment of the metal particle is not particularly limited, and commonly used surface treatment techniques can be applied. Examples of treatment methods include an oil treatment with hydrocarbon oil, ester oil, lanolin, or the like; a silicone treatment with dimethylpolysiloxane, methylhydrogenpolysiloxane, methylphenylpolysiloxane, or the like; a fluorine compound treatment with perfluoroalkyl group-containing ester, perfluoroalkylsilane, perfluoropolyether, perfluoroalkyl group-containing polymer, or the like; a silane coupling agent treatment with 3-methacryloxypropyltrimethoxysilane, 3-glycidoxypropyltrimethoxysilane, or the like; a titanate coupling agent treatment with isopropyl triisostearoyl titanate, isopropyltris (dioctylpyrophosphate)titanate, or the like; a metallic soap treatment; an amino acid treatment with acylglutamic acid or the like; a lecithin treatment with hydrogenated egg yolk lecithin or the like; a collagen treatment; a polyethylene treatment; a moisturizing treatment; an inorganic compound treatment; and a mechanochemical treatment.

There is no particular limitation on a metal constituting the metal particle. The metal may be a metal atom alone or may be a carbide (for example, tungsten carbide (WC)), a nitride, an oxide or a boride of the metal atom. In addition, the metal may form an alloy. Examples of the alloy include high-tensile steel (Fe—C), chromium molybdenum steel (Fe—Cr—Mo), manganese molybdenum steel (Fe—Mn—Mo), stainless steel (Fe—Ni—Cr), 42 alloy, Invar (Fe—Ni), permendur (Fe—Co), silicon steel (Fe—Si), red brass, tombac (Cu—Zn), German silver (Cu—Zn—Ni), bronze (Cu—Sn), cupronickel (Cu—Ni), shakudo (Cu—Au), constantan (Cu—Ni), duralumin (Al—Cu), Hastelloy (Ni—Mo—Cr—Fe), Monel (Ni—Cu), Inconel (Ni—Cr—Fe), nichrome (Ni—Cr), ferromanganese (Mn—Fe), and cemented carbide (WC/Co).

The metal atom constituting the metal particle preferably includes at least one of metal elements of Group 4 to Group 13 of the Periodic Table from the viewpoint of general-purpose properties and ease of surface modification, and more preferably includes at least one of metal elements of Group 6 or Group 8 of the Periodic Table from the viewpoint of general-purpose properties and surface modification.

The metal atom still more preferably includes at least one of Zn, In, Au, Ag, Co, Zr, W, Ta, Fe, Cu, Ni, Nb, Pt, Mn, or Mo from the viewpoint of general-purpose properties and surface modification, and even still more preferably includes at least one of Fe, Mo, or W from the viewpoint of general-purpose properties.

The particle diameter of the metal particle used in the present invention is preferably 0.01 to 100 μm and more preferably 1 to 10 μm, from the viewpoint of dispersion stability in a composition for forming the acoustic matching sheet according to the embodiment of the present invention which will be described later and improvement of acoustic wave sensitivity of the sheet according to the embodiment of the present invention. The "particle diameter" of the metal particle refers to an average primary particle diameter.

Here, the average primary particle diameter refers to a volume average particle diameter. The volume average particle diameter is determined as follows.

The metal particles are added to methanol at a concentration of 0.5% by mass, and subjected to ultrasonic waves for 10 minutes to disperse the metal particles. The particle size distribution of the metal particles thus treated is measured by a laser diffraction/scattering-type particle size distribution analyzer (trade name: LA950V2, manufactured by HORIBA, Ltd.), and the volumetric median diameter of the measured metal particles is defined as the volume average particle diameter. The median diameter corresponds to a particle size at 50% in the particle size distribution represented in cumulative form.

The content of each of the components (A) and (B) in the sheet according to the embodiment of the present invention is not particularly limited as long as each component can be produced by various methods, and is appropriately adjusted according to the desired acoustic impedance and the like.

In addition, the content of each of the components (A) to (C) in the sheet according to the embodiment of the present invention is also appropriately adjusted according to the desired acoustic impedance and the like. For example, in a case where the acoustic matching layer is made into a multi-layer structure, it may be configured such that the content of the component (C) in the sheet used for the acoustic matching layer on the piezoelectric element side is relatively high, and the content of the component (C) in the sheet used for the acoustic matching layer on the acoustic lens side is relatively low; or the component (C) is not used. Such a configuration makes it possible to provide a gradient of the acoustic impedance from the piezoelectric element side to the acoustic lens side, which can therefore make the propagation of the acoustic wave more efficient.

Specifically, the contents of the components (A) to (C) can be appropriately determined within the following ranges.

The content of the component (B): preferably 1 to 60 parts by mass, more preferably 3 to 50 parts by mass, and still more preferably 5 to 40 parts by mass with respect to 100 parts by mass of the content of the component (A).

The content of the component (C): preferably 300 to 1050 parts by mass, more preferably 350 to 1000 parts by mass, and still more preferably 400 to 950 parts by mass with respect to 100 parts by mass of the content of the component (A).

In addition, the content of the component (B) is preferably 0.5 parts by mass or more, more preferably 1.5 parts by mass or more, still more preferably 2.5 parts by mass or more, and even still more preferably 3.5 parts by mass or more with respect to 100 parts by mass of the component (C). The upper limit of the content of the component (B) is preferably 10 parts by mass or less, more preferably 8 parts by mass or less, and still more preferably 6 parts by mass or less.

The sheet according to the embodiment of the present invention may be composed of the component (A) and the component (B), or may be composed of the component (A), the component (B), and the component (C), In addition, components other than these may also be contained as long as the effects of the present invention are not impaired. As components other than the component (A) and the component (B) and other than the component (C) (other components), for example, at least one of a curing retarder, a dispersant, a pigment, a dye, an antistatic agent, an antioxidant, a flame retardant, or a thermal conductivity improver can be appropriately added.

In the sheet according to the embodiment of the present invention, the sum of the contents of the component (A), the component (B), and the component (C) is preferably 80% by mass or more and more preferably 90% by mass or more.

The composition for an acoustic matching layer according to the embodiment of the present invention (hereinafter, also referred to as "the composition according to the embodiment of the present invention") contains the following components (A1) and (B1).

(A1): at least one of a resin or a rubber.
(B1): at least one of a resin particle or a rubber particle having an acoustic velocity lower than an acoustic velocity of the component (A1) and having a number average particle diameter of 1.0 μm or less.

Examples of the resin of the component (A1) include the resin and rubber mentioned in the (A) above. However, in a case where the component (A1) is a thermosetting resin or rubber, the component (A1) is not limited to the cured state, and may be in the state before curing. That is, the composition according to the embodiment of the present invention may be a composition for forming an acoustic matching sheet. In this case, the components (A1) and (B1) may be in a state of being dissolved or dispersed in a solvent. As the component (B1), the above-mentioned component (B) can be adopted.

In addition, the composition according to the embodiment of the present invention may contain the above-mentioned component (C) or may contain the above-mentioned other components.

<Component (D)>

The composition according to the embodiment of the present invention may contain a curing agent as the component (D) depending on the type of the component (A1).

For example, in a case where an epoxy resin is used as the component (A1), the composition according to the embodiment of the present invention preferably contains a polyamine compound. In addition, in a case where a rubber is contained as the component (A1) and the rubber is cured (crosslinked), the composition according to the embodiment of the present invention preferably contains an organic peroxide.

The acoustic matching sheet according to the embodiment of the present invention can be obtained by forming the composition according to the embodiment of the present invention into a sheet and, if necessary, cutting or dicing the sheet to a desired thickness or shape. This acoustic matching sheet is used as an acoustic matching layer of an acoustic wave probe. The configuration of the acoustic wave probe including the acoustic matching layer will be described later. The composition according to the embodiment of the present invention may be in the form of a material set for an acoustic matching sheet in which the main agent including the component (A1) and the component (B1) and the curing agent of the component (D) are separately separated. In the present invention, the term "composition" is used in a broader sense than usual. That is, such a set form is also included in the composition in the present invention. In forming the acoustic matching sheet, the main agent and the curing agent can be mixed and used to form the acoustic matching sheet.

In the production of the sheet, in a case where the composition according to the embodiment of the present invention contains a thermosetting component, it is preferable that the composition is formed into a desired sheet in a low temperature range where a curing reaction does not occur or a curing rate is slow, and then the formed product is cured by heating or the like if necessary to obtain an acoustic matching sheet or a precursor sheet thereof. That is, in this case, the acoustic matching sheet according to the embodiment of the present invention is a cured substance obtained by curing the composition according to the embodiment of the present invention to form a three-dimensional network structure.

In a case where the composition according to the embodiment of the present invention does not contain a thermosetting component, the sheet is preferably produced by various methods such as injection molding and coating molding depending on the material.

(Polyamine Compound)

The polyamine compound used in the present invention preferably includes at least one polyamine compound represented by General Formula (I) as a curing component that acts on an epoxy resin to cure.

$$L(-NH_2)_n \qquad \text{General Formula (I)}$$

In General Formula (I), n represents an integer of 2 to 20 (preferably 3 to 20), L represents an n-valent aliphatic hydrocarbon group in which at least one oxygen atom is incorporated in the aliphatic hydrocarbon chain, or an n-valent group having an aromatic ring and aliphatic hydrocarbon group containing at least one oxygen atom.

The polyamine compound preferably includes at least one polyamine compound represented by any of General Formulae (II), (III), and (IV).

$$L^1 \!\!-\!\!\left[\!\!\left(O\!-\!L^2\right)_{\!s}\!\!-\!NH_2\right]_{n1} \qquad \text{General Formula (II)}$$

In General Formula (II), s represents an integer of 1 to 100, and n1 represents an integer of 2 to 20. $L^1$ represents an n1-valent aliphatic hydrocarbon group having 1 to 20 carbon atoms or an n1-valent aromatic hydrocarbon group having 6 to 20 carbon atoms, and $L^2$ represents an aliphatic hydrocarbon chain having 2 to 6 carbon atoms.

The aliphatic hydrocarbon group and the aliphatic hydrocarbon chain may be linear or branched.

s is preferably an integer of 1 to 50 and more preferably an integer of 2 to 20.

n1 is preferably an integer of 1 to 15, more preferably an integer of 2 to 6, and still more preferably 3 or 4.

The aliphatic hydrocarbon group represented by $L^1$ is preferably an n1-valent aliphatic hydrocarbon group having 2 to 15 carbon atoms, more preferably an n1-valent aliphatic hydrocarbon group having 3 to 10 carbon atoms, and still more preferably an n1-valent aliphatic hydrocarbon group having 5 or 6 carbon atoms.

The aromatic hydrocarbon group represented by $L^1$ is preferably an n1-valent aromatic hydrocarbon group having 6 to 15 carbon atoms, more preferably an n1-valent aromatic hydrocarbon group having 6 to 10 carbon atoms, and more preferably an n1-valent benzene.

$L^2$ is more preferably an aliphatic hydrocarbon chain having 2 to 4 carbon atoms and still more preferably an aliphatic hydrocarbon chain having 2 or 3 carbon atoms.

General Formula (III)

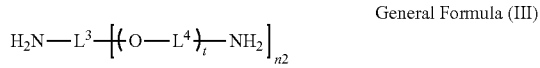

In General Formula (III), t represents an integer of 1 to 100, and n2 represents an integer of 1 to 19. $L^3$ represents an (n2+1)-valent aliphatic hydrocarbon group having 1 to 20 carbon atoms or an (n2+1)-valent aromatic hydrocarbon group having 6 to 20 carbon atoms, and $L^4$ represents an aliphatic hydrocarbon chain having 2 to 6 carbon atoms.

In order to further improve the breaking energy of the acoustic matching layer and further reduce the variation in acoustic characteristics, t is preferably an integer of 1 to 50 and more preferably an integer of 2 to 20.

n2 is preferably an integer of 2 to 19, more preferably an integer of 2 to 5, and still more preferably 3.

The aliphatic hydrocarbon group represented by $L^3$ is preferably an (n2+1)-valent aliphatic hydrocarbon group having 2 to 10 carbon atoms, more preferably an (n2+)-valent aliphatic hydrocarbon group having 2 to 6 carbon atoms, and still more preferably an (n2+1)-valent aliphatic hydrocarbon group having 2 to 4 carbon atoms.

The aromatic hydrocarbon group represented by $L^3$ is preferably an (n2+1)-valent aromatic hydrocarbon group having 6 to 15 carbon atoms, more preferably an (n2+1)-valent aromatic hydrocarbon group having 6 to 10 carbon atoms, and more preferably an (n2+1)-valent benzene.

$L^4$ is more preferably an aliphatic hydrocarbon chain having 2 to 4 carbon atoms and still more preferably an aliphatic hydrocarbon chain having 2 or 3 carbon atoms.

General Formula (IV)

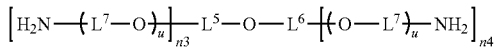

In General Formula (IV), u represents an integer of 1 to 100, n3 and n4 represent an integer of 1 or more, and the sum of n3 and n4 is 20 or less. $L^5$ represents an (n3+1)-valent aliphatic hydrocarbon group having 1 to 20 carbon atoms or an (n3+1)-valent aromatic hydrocarbon group having 6 to 20 carbon atoms. IP represents an (n4+1)-valent aliphatic hydrocarbon group having 1 to 20 carbon atoms or an (n4+1)-valent aromatic hydrocarbon group having 6 to 20 carbon atoms. $L^7$ represents an aliphatic hydrocarbon chain having 2 to 6 carbon atoms.

u is preferably an integer of 1 to 50 and more preferably an integer of 2 to 20.

n3 and n4 are preferably an integer of 2 to 10, more preferably an integer of 2 to 5, and still more preferably 2 or 3.

The aliphatic hydrocarbon group represented by $L^5$ is preferably an (n3+1)-valent aliphatic hydrocarbon group having 2 to 15 carbon atoms, more preferably an (n3+1)-valent aliphatic hydrocarbon group having 2 to 10 carbon atoms, and still more preferably an (n3+1)-valent aliphatic hydrocarbon group having 3 to 6 carbon atoms.

The aromatic hydrocarbon group represented by $L^5$ is preferably an (n3+1)-valent aromatic hydrocarbon group having 6 to 15 carbon atoms, more preferably an (n3+1)-valent aromatic hydrocarbon group having 6 to 10 carbon atoms, and still more preferably an (n3+1)-valent benzene.

The aliphatic hydrocarbon group represented by $L^6$ is preferably an (n4+1)-valent aliphatic hydrocarbon group having 2 to 15 carbon atoms, more preferably an (n4+1)-valent aliphatic hydrocarbon group having 2 to 10 carbon atoms, and still more preferably an (n4+1)-valent aliphatic hydrocarbon group having 3 to 6 carbon atoms.

The aromatic hydrocarbon group represented by $L^6$ is preferably an (n4+1)-valent aromatic hydrocarbon group having 6 to 15 carbon atoms, more preferably an (n4+1)-valent aromatic hydrocarbon group having 6 to 10 carbon atoms, and still more preferably an (n4+1)-valent benzene.

$L^7$ is more preferably an aliphatic hydrocarbon chain having 2 to 4 carbon atoms and still more preferably an aliphatic hydrocarbon chain having 2 or 3 carbon atoms.

The polyamine compound used in the present invention may have the following substituent T as long as the effects of the present invention are not impaired.

Examples of the substituent T include the following: an alkyl group (preferably having 1 to 20 carbon atoms), an alkenyl group (preferably having 2 to 20 carbon atoms), an alkynyl group (preferably having 2 to 20 carbon atoms), a cycloalkyl group (preferably having 3 to 20 carbon atoms; provided that the term alkyl group in the present invention usually means to include a cycloalkyl group), an aryl group (preferably having 6 to 26 carbon atoms), aralkyl group (preferably having 7 to 23 carbon atoms), a heterocyclic group (preferably a heterocyclic group having 2 to 20 carbon atoms, and more preferably 5- or 6-membered heterocyclic group having at least one oxygen atom, sulfur atom or nitrogen atom), an alkoxy group (preferably having 1 to 20 carbon atoms), an aryloxy group (preferably having 6 to 26 carbon atoms; provided that the term alkoxy group in the present invention usually means to include an aryloxy group), an alkoxycarbonyl group (preferably having 2 to 20 carbon atoms), an aryloxycarbonyl group (preferably having 6 to 26 carbon atoms), an amino group (including an amino group, an alkylamino group, and an arylamino group each preferably having 0 to 20 carbon atoms), a sulfamoyl group (preferably having 0 to 20 carbon atoms), an acyl group (preferably having 1 to 20 carbon atoms), an aryloyl group (preferably having 7 to 23 carbon atoms; provided that the term acyl group in the present invention usually means to include an aryloyl group), an acyloxy group (preferably having 1 to 20 carbon atoms), an aryloyloxy group (preferably having 7 to 23 carbon atoms; provided that the term acyloxy group in the present invention usually means to include an aryloyloxy group), a carbamoyl group (preferably having 1 to 20 carbon atoms), an acylamino group (preferably having 1 to 20 carbon atoms), an alkylthio group (preferably having 1 to 20 carbon atoms), an arylthio group (preferably having 6 to 26 carbon atoms), an alkylsulfonyl group (preferably having 1 to 20 carbon atoms), an arylsulfonyl group (preferably having 6 to 22 carbon atoms), an alkylsilyl group (preferably having 1 to 20 carbon atoms), an arylsilyl group (preferably having 6 to 42 carbon atoms), an alkoxysilyl group (preferably having 1 to 20 carbon atoms), an aryloxysilyl group (preferably having 6 to 42 carbon atoms), a phosphoryl group (preferably a phosphoryl group having 0 to 20 carbon atoms, for example —OP(=O)(R$^P$)$_2$), a phosphonyl group (preferably a phosphonyl group having 0 to 20 carbon atoms, for example, —P(=O)(R$^P$)$_2$), a phosphinyl group (preferably a phosphinyl group having 0 to 20 carbon atoms, for example, —P(=O)(R$^P$)$_2$), a (meth)acryloyl group, a (meth)acryloyloxy group, a (meth)acryloylimino group ((meth)acrylamide group), a hydroxy group, a sulfanyl group, a carboxy group, a phosphate group, a phosphonate group, a sulfonate group, a cyano group, and a halogen atom (for example, a fluorine atom, a chlorine atom, a bromine atom, or an iodine atom). R$^P$ is a hydrogen atom, a hydroxy group, or a substituent (preferably a group selected from the substituent T).

In addition, each group listed in the substituent T may be further substituted with the above-mentioned substituent.

In a case where the compound, substituent, linking group, and the like contain an alkyl group, an alkylene group, an alkenyl group, an alkenylene group, an alkynyl group, an alkynylene group, and the like, these groups may be cyclic or chain-like, may be linear or branched, and may be substituted or unsubstituted as described above.

Hereinafter, specific examples of the polyamine compound used in the present invention will be shown, but the present invention is not limited thereto.

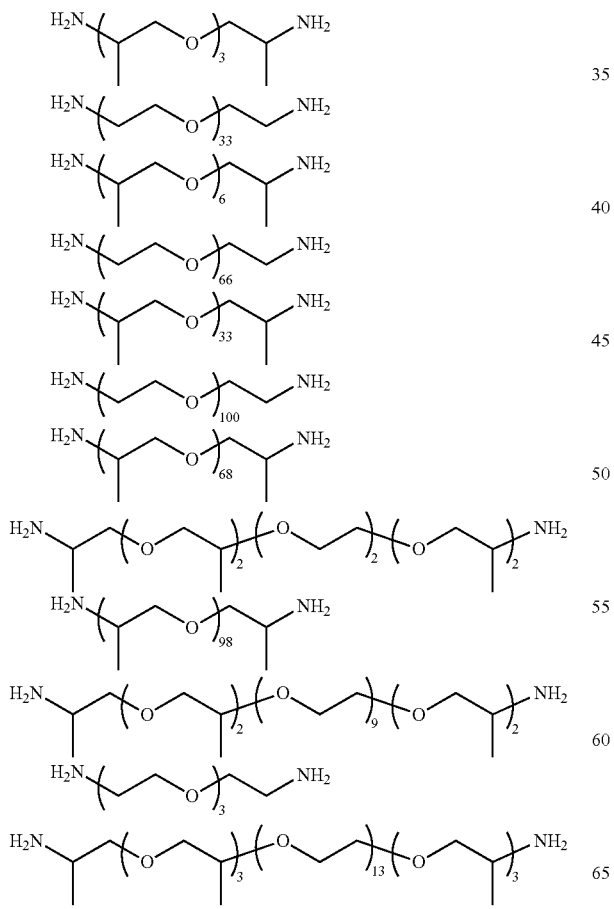
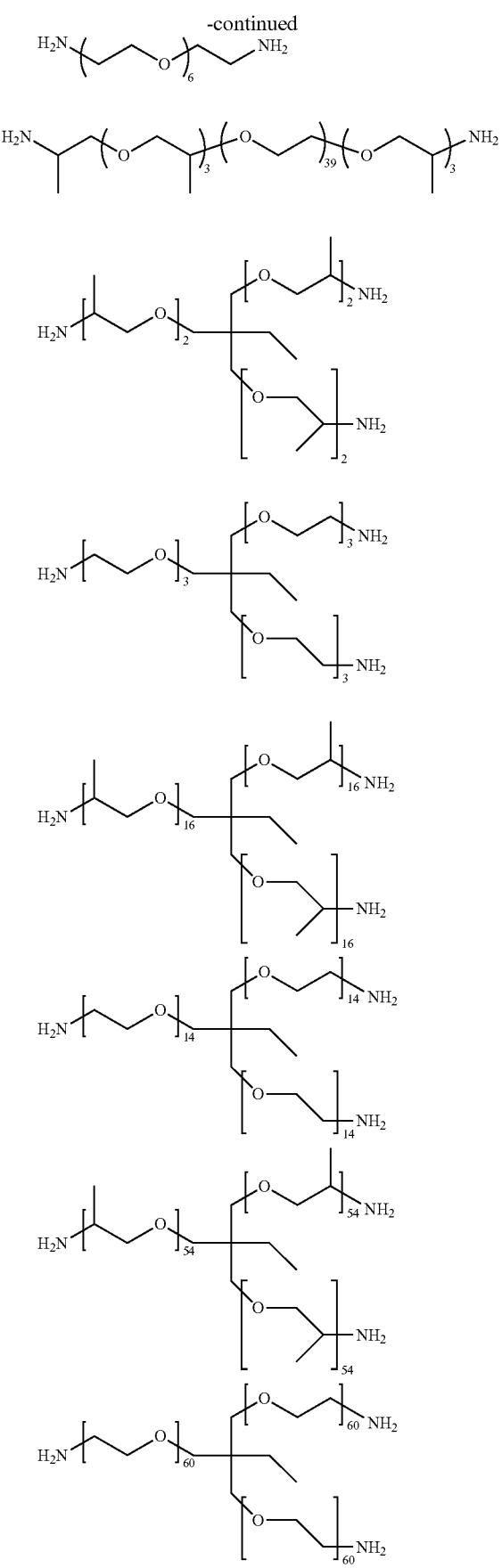

-continued
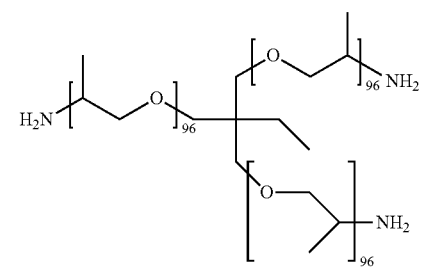
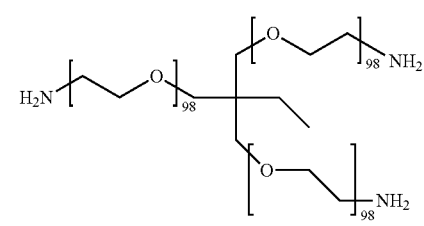
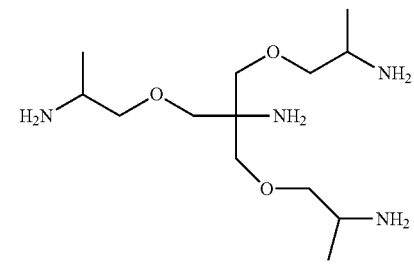
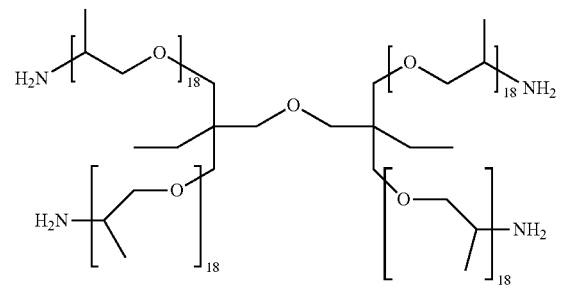
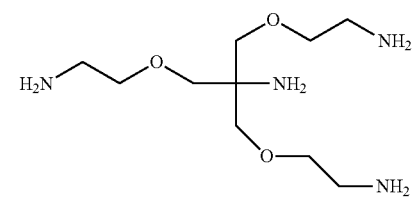
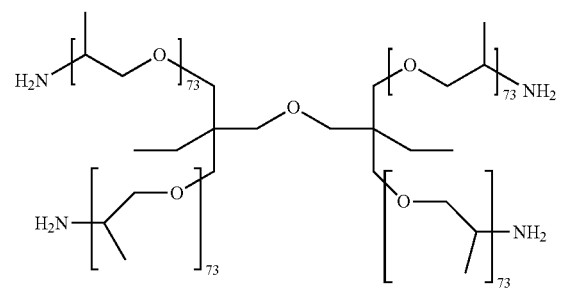
-continued
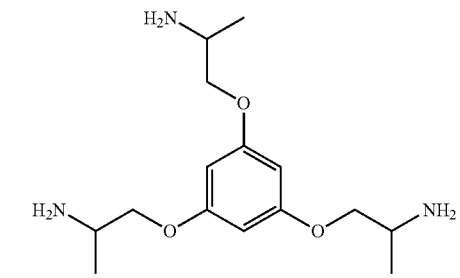
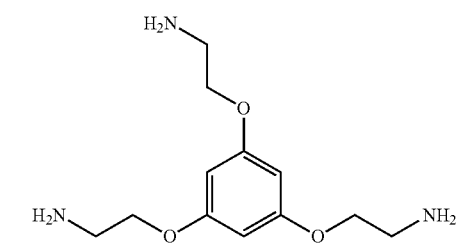
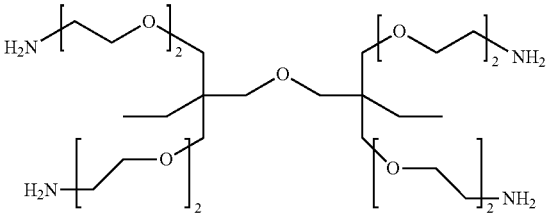
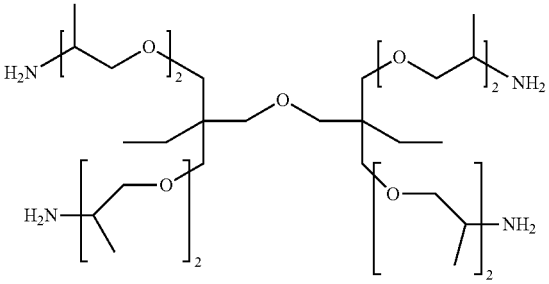
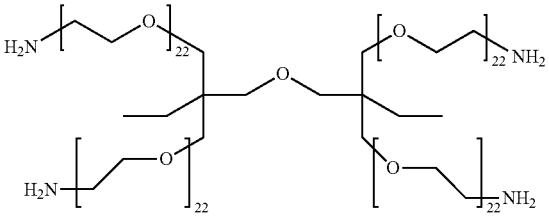
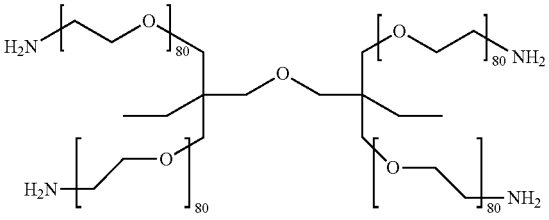
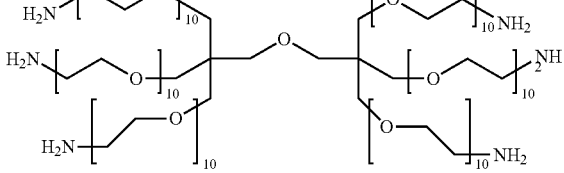

-continued

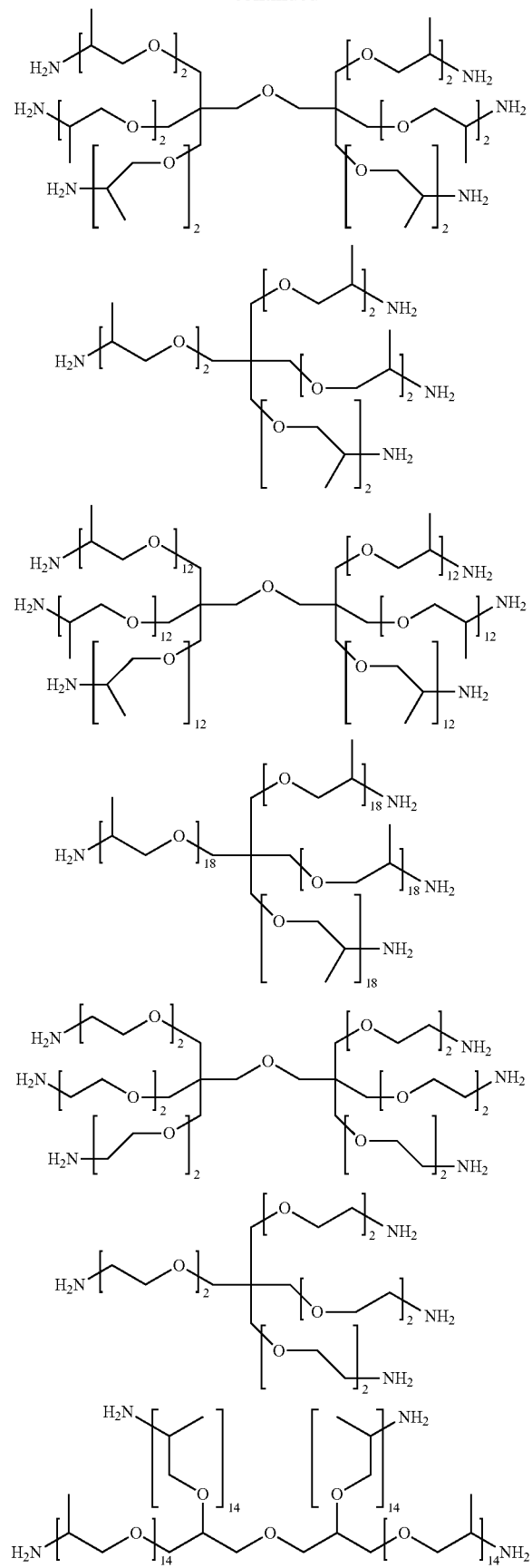

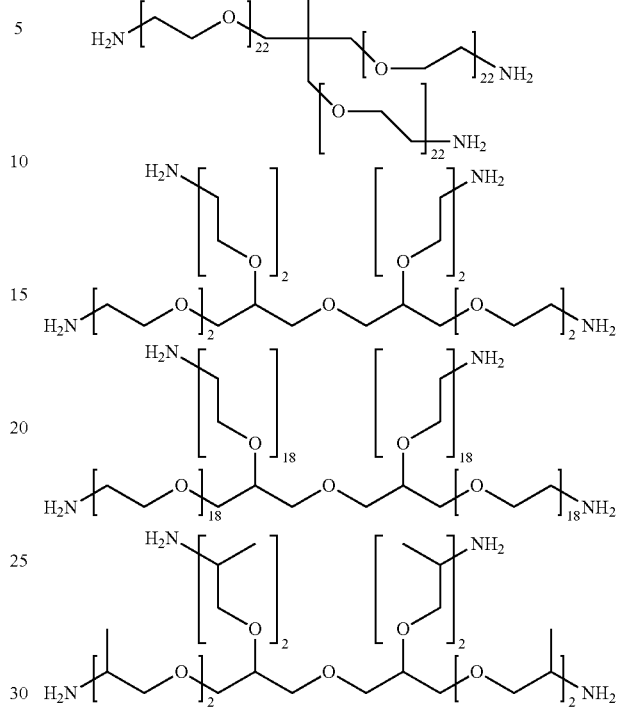

The polyamine compound used in the present invention can be synthesized by a conventional method. In addition, a commercially available product may be used as the polyamine compound.

The polyamine compound may consist of the polyamine compound represented by General Formula. (I), or may include, in addition to the above polyamine compound, other amine compounds (for example, a tertiary amine compound) as long as the effects of the present invention are not impaired. The content of the polyamine compound represented by General Formula (I) in the polyamine compound is preferably 80% by mass or more and more preferably 90% by mass or more.

In the composition according to the embodiment of the present invention, the equivalent ratio of the epoxy resin to the polyamine compound can be, for example, epoxy resin/polyamine compound (number of moles of epoxy group/number of moles of amino group×2 (number of moles of active hydrogen))=0.5/1 to 1/0.5.

In addition, in a case where the composition according to the embodiment of the present invention is prepared by mixing the main agent and the curing agent at the time of sheet formation using the above-mentioned material set for an acoustic matching sheet, preferred is a form in which the main agent and the curing agent are mixed and used such that the mass ratio of the epoxy resin to the polyamine compound is 99/1 to 20/80 of the epoxy resin/polyamine compound; and more preferred is a form in which the main agent and the curing agent are mixed and used such that the mass ratio of the epoxy resin to the polyamine compound is 90/10 to 40/60 of the epoxy resin/polyamine compound.

(Organic Peroxide)

Examples of the organic peroxide used in the present invention include commonly used organic peroxides such as a hydroperoxide, a dialkyl peroxide, a peroxyester, a diacyl peroxide, and a peroxyketal, which have at least a carbon atom and an —O—O— bond in the molecule.

Specifically, the following organic peroxides can be mentioned.

Hydroperoxides: p-menthane hydroperoxide, diisopropylbenzene hydroperoxide, 1,1,3,3-tetramethylbutyl hydroperoxide, cumene hydroperoxide, t-butyl hydroperoxide, and the like Dialkyl peroxides: 1,3-bis(2-t-butylperoxyisopropyl)benzene, dicumyl peroxide, 2,5-dimethyl-2,5-di(t-butylperoxy)hexane, t-butylcumyl peroxide, di-t-hexyl peroxide, di-t-butyl peroxide, 2,5-bis(t-butylperoxy)-2,5-dimethyl-3-hexine, and the like Peroxyesters: t-butyl peroxybenzoate, t-butyl peroxymaleate, t-butyl peroxy-3,5,5-trimethylhexanoate, t-butyl peroxylaurate, t-butyl peroxy isopropyl monocarbonate, t-butyl peroxy-2-ethylhexyl monocarbonate, t-hexyl peroxybenzoate, 2,5-bis(benzoylperoxy)-2,5-dimethylhexane, t-butyl peroxyacetate, and the like Diacyl peroxides: bis(3-methylbenzoyl)peroxide, benzoyl (3-methylbenzoyl)peroxide, dibenzoyl peroxide, bis(4-methylbenzoyl)peroxide, and the like Peroxyketals: 1,1-bis(t-hexylperoxy)-3,3,5-trimethylcyclohexane, 1,1-bis(t-hexylperoxy)cyclohexane, 1,1-bis(t-butylperoxy)-2-methylcyclohexane, 1,1-bis(t-butylperoxy) cyclohexane, 2,2-bis(t-buty peroxy)butane, n-butyl 4,4-bis (t-butylperoxy)valerate, 2,2-bis(4,4-bis(t-butylperoxy) cyclohexyl)propane, and the like The organic peroxides may be used alone or in combination of two or more thereof. In addition, the content of the organic peroxide in the composition according to the embodiment of the present invention can be, for example, 20 parts by mass or less, preferably 15 parts by mass or less, and more preferably 10 parts by mass or less with respect to 100 parts by mass of the content of the component (A). The lower limit of the content of the organic peroxide is not particularly limited, but it is practically 0.1 parts by mass or more.

<Preparation of Composition for Acoustic Matching Layer>

The composition for an acoustic matching layer according to the embodiment of the present invention can be obtained, for example, by kneading the components constituting the composition for an acoustic matching layer using a kneader, a pressure kneader, a Banbury mixer (continuous kneader), a two-roll kneading device, or the like. As a result, it is possible to obtain a composition for an acoustic matching layer in which the components (A1) and (B1) are dispersed.

In a case where an epoxy resin is used as the component (A1) and a polyamine compound is used as the curing agent, the curing reaction of the epoxy resin may proceed over time in the composition according to the embodiment of the present invention. Therefore, the properties of this composition change over time and may not be stable. However, for example, by mixing and storing the above composition at a temperature of −10° C. or lower, the composition in a state in which each component is stably maintained can be obtained without causing a curing reaction or sufficiently suppressing the curing reaction.

In addition, in the case of making a material set for an acoustic matching sheet containing a main agent consisting of the components (A1) and (B1) and a curing agent, the main agent can be obtained by kneading the components (A1) and (B1). In a case of producing an acoustic matching sheet, the composition according to the embodiment of the present invention is prepared by mixing this main agent and a curing agent, and the composition is cured while being formed, whereby an acoustic matching sheet or a precursor sheet thereof can be formed.

The kneading and forming are preferably carried out while removing air bubbles, and therefore are usually carried out under reduced pressure.

In addition, the temperature condition for kneading is preferably 5° C. to 40° C. and more preferably 10° C. to 30° C.

[Acoustic Wave Probe]

The acoustic wave probe according to the embodiment of the present invention has the sheet according to the embodiment of the present invention as an acoustic matching layer. The acoustic matching layer may have a multi-layer structure in which a plurality of sheets according to the embodiment of the present invention are laminated. In this multi-layer structure, it is preferable that the acoustic impedance exhibits a gradient from the piezoelectric element side to the acoustic lens side so as to be close to the value of the living body. The number of sheets to be laminated and the thickness of each sheet can be appropriately adjusted according to the thickness of the acoustic matching layer itself to be formed. The number of sheets can be, for example, 2 to 50 and preferably 3 to 20. The thickness of each sheet according to the embodiment of the present invention is, for example, 1 to 500 μm.

An example of the configuration of the acoustic wave probe according to the embodiment of the present invention is shown in the FIG. The acoustic wave probe shown in the FIG. is an ultrasound probe in an ultrasound diagnostic apparatus. The ultrasound probe is a probe which particularly uses an ultrasonic wave as an acoustic wave in an acoustic wave probe. For this reason, a basic configuration of the ultrasound probe can be applied to the acoustic wave probe as it is.

<Ultrasound Probe>

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end portion (the surface coming into contact with a living body which is a test object) as shown in the FIG. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

(Piezoelectric Element Layer)

The piezoelectric element layer 3 is a portion which generates an ultrasonic wave and in which an electrode is attached to both sides of a piezoelectric element. In a case where a voltage is applied to the electrode, the piezoelectric element layer generates an ultrasonic wave through repeated contraction and expansion of the piezoelectric element and through vibration.

A so-called ceramics inorganic piezoelectric body obtained by a polarization treatment of a quartz crystal, a single crystal such as $LiNbO_3$, $LiTaO_3$, or $KNbO_3$, a thin film of ZnO or AlN, a $Pb(Zr,Ti)O_3$-based sintered body, or the like is widely used as the material constituting a piezoelectric element. In general, piezoelectric ceramics such as lead zirconate titanate (PZT) with good conversion efficiency are used.

In addition, wider bandwidth sensitivity is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using a micro electro mechanical systems (MEMS) technology in which an array structure, which shows excellent short pulse characteristics, excellent wideband characteristics, and excellent mass productivity and has less characteristic variations, is obtained is disclosed in JP2011-071842A or the like.

In the present invention, it is possible to preferably use any piezoelectric element material (Backing Material)

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

(Acoustic Matching Layer)

The acoustic matching layer 2 is provided in order to reduce the difference in acoustic impedance between the piezoelectric element layer 3 and a test object and to efficiently transmit and receive an ultrasonic wave.

(Acoustic Lens)

The acoustic lens 1 is provided in order to improve resolution by making an ultrasonic wave converge in a slice direction using refraction. In addition, it is necessary for the acoustic lens to achieve matching of an ultrasonic wave with acoustic impedance (1.4 to $1.7 \times 10^6$ kg/m$^2$/sec in a case of a human body) of a living body which is a test object after being closely attached to the living body and to reduce ultrasonic attenuation of the acoustic lens 1 itself.

That is, sensitivity of transmission and reception of an ultrasonic wave is increased using a material of which the acoustic velocity is sufficiently lower than that of a human body, the ultrasound attenuation is low, and the acoustic impedance is close to a value of the skin of a human body, as the material of the acoustic lens 1.

The operation of the ultrasound probe 10 having such a configuration will be described. The piezoelectric element layer 3 is resonated after applying a voltage to the electrodes provided on both sides of a piezoelectric element, and an ultrasonic signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

[Method for Manufacturing Acoustic Wave Probe]

The acoustic wave probe according to the embodiment of the present invention can be produced by a conventional method, except that the composition according to the embodiment of the present invention is used. That is, the method for manufacturing an acoustic wave probe according to the embodiment of the present invention includes forming an acoustic matching layer on a piezoelectric element using the composition according to the embodiment of the present invention. The piezoelectric element can be provided on the backing material by a conventional method.

In addition, an acoustic lens is formed on the acoustic matching layer by a conventional method using a material for forming the acoustic lens.

[Acoustic Wave Measurement Apparatus]

The acoustic wave measurement apparatus according to the embodiment of the present invention has the acoustic wave probe according to the embodiment of the present invention. The acoustic wave measurement apparatus has a function of displaying the signal intensity of a signal received by the acoustic wave probe and imaging the signal.

It is also preferable that the acoustic wave measurement apparatus according to the embodiment of the present invention is an ultrasonic wave measurement apparatus using an ultrasound probe.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like. Hereinafter, the room temperature means 25° C.

Synthesis Example

<1> Preparation of composition for acoustic matching layer (1) Preparation of Composition for Acoustic Matching Layer Used in Example 1

100 parts by mass of metal particles (iron powder (Fe)) (EW-I, trade name, manufactured by BASF SE)), 11 parts by mass of an epoxy resin (bisphenol A diglycidyl ether ("jER825", trade name, manufactured by Mitsubishi Chemical Corporation, epoxy equivalent: 170)), and 4 parts by mass of polybutadiene particles were defoamed for 4 minutes while stirring at 1800 rpm in a state where the pressure was reduced to 1.0 Pa at room temperature with "AWATORI RENTARO ARV-310 (trade name, manufactured by Thinky Corporation)". After that, 10 parts by mass of a curing agent (D-1) represented by the chemical formula described later was defoamed for 4 minutes while stirring at 1800 rpm in a state Where the pressure was reduced to 1.0 Pa at room temperature with "AWATORI RENTARO ARV-310 (trade name, manufactured by Thinky Corporation)", thereby preparing a composition for an acoustic matching layer used in Example 1.

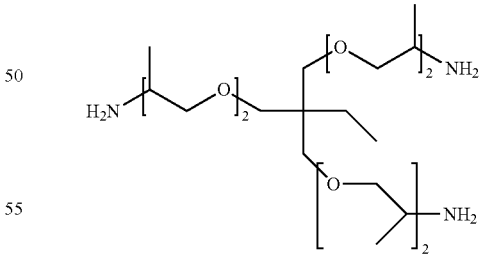

(2) Preparation of Composition for Acoustic Matching Layer Used in Examples 2 to 34 and Comparative Examples 1 to 11

The composition for an acoustic matching layer used in each of Examples 2 to 34 and Comparative Examples 1 to 11 was prepared in the same manner as in the preparation of the composition for an acoustic matching layer used in Example 1, except that the composition was changed to the composition shown in Table 1 below (3) Preparation of Composition for Acoustic Matching Layer Used in Example 35

100 parts by mass of metal particles (iron powder (Fe) (EW-I, trade name, manufactured by BASF SE)), 11 parts by mass of a polyamide resin (nylon 12, manufactured by Kureha Extron Co., Ltd.), and 4 parts by mass of polybutadiene particles were extruded and kneaded (280° C.) with a kneader to prepare a composition for an acoustic matching layer used in Example 35.

(4) Preparation of Composition for Acoustic Matching Layer Used in Examples 36 to 41 and Comparative Examples 12 to 15.

The composition for an acoustic matching layer used in each of Examples 36 to 41 and Comparative Examples 12 to 15 was prepared in the same manner as in the preparation of the composition for an acoustic matching layer used in Example 35, except that the composition was changed to the composition shown in Table 1 below (5) Preparation of Composition for Acoustic Matching Layer Used in Example 42

100 parts by mass of metal particles (iron powder (Fe) (EW-I, trade name, manufactured by BASF SE)), 11 parts by mass of polyisoprene rubber ("Nipol IR2200", trade name, manufactured by Zeon Corporation), 1 part by mass of dicumyl peroxide (PERCUMYL D-40, manufactured by NOF Corporation), and 4 parts by mass of polybutadiene particles were kneaded with a LABO PLASTOMILL at 80° C. to prepare a composition for an acoustic matching layer used in Example 42.

(6) Preparation of Composition for Acoustic Matching Layer Used in Examples 43 to 48 and Comparative Examples 16 to 21

The composition for an acoustic matching layer used in each of Examples 43 to 48 and Comparative Examples 16 to 21 was prepared in the same manner as in the preparation of the composition for an acoustic matching layer used in Example 42, except that the composition was changed to the composition shown in Table 1 below.

<2> Production of Acoustic Matching Sheet (1) Production of Acoustic Matching Sheet of Example 1

An acoustic matching sheet was produced by pouring the prepared composition for an acoustic matching layer into a mold having a length of 5 cm, a width of 5 cm, and a height of 2 mm and curing the composition at 60° C. for 18 hours and then at 150° C. for 1 hour.

(2) Production of Acoustic Matching Sheet of Examples 2 to 34 and Comparative Examples 1 to 11

An acoustic matching sheet was produced in the same manner as in the production of the acoustic matching sheet of Example 1, except that the composition for an acoustic matching layer used in each of Examples 2 to 34 and Comparative Examples 1 to 11 was used instead of the composition for an acoustic matching layer used in Example 1, (3) Production of Acoustic Matching Sheet of Example 35

The composition for an acoustic matching layer used in Example 1 was set in a mold having a length of 5 cm, a width of 5 cm, and a height of 2 min, pressed at the melting point of the component (A)+10° C. for 5 minutes, and cooled to produce an acoustic matching sheet, (4) Production of Acoustic Matching Sheet of Examples 36 to 41 and Comparative Examples 12 to 15

An acoustic matching sheet was produced in the same manner as in the production of the acoustic matching sheet of Example 35, except that the composition for an acoustic matching layer used in each of Examples 36 to 41 and Comparative Examples 12 to 15 was used instead of the composition for an acoustic matching layer used in Example 35.

(5) Production of Acoustic Matching Sheet Used in Example 42

The composition for an acoustic matching layer used in Example 42 was set in a mold having a length of 5 can, a width of 5 can, and a height of 2 mm, and pressed at a temperature of 120° C. for 30 minutes to produce an acoustic matching sheet.

(6) Production of Acoustic Matching Sheet Used in Examples 43 to 48 and Comparative Examples 16 to 21

An acoustic matching sheet was produced in the same manner as in the production of the acoustic matching sheet of Example 42, except that the composition for an acoustic matching layer used in each of Examples 43 to 48 and Comparative Examples 16 to 21 was used instead of the composition for an acoustic matching layer used in Example 42.

Test Example

<1> Measurement of Acoustic Velocity (1) Acoustic Velocity of Component (A)

The acoustic velocity of the component (A) was calculated by calculating a local elastic modulus of the component (A) with a scanning probe microscope (SPM-9700, trade name, manufactured by Shimadzu Corporation) by the JKR theory, and using the density of the component (A) by the following equation. The local elastic modulus was calculated by pushing a cantilever against the acoustic matching sheet to a depth of 5 nm. The density was determined in such a manner that a small amount of the component (A) was taken out from the acoustic matching sheet and analyzed as a sample with an analysis apparatus such as NMR, IR, or pyrolysis GC-MS to clarify the composition, and the density was determined based on this composition.

$$\text{Acoustic velocity} = (\text{local elastic modulus/density})^{1/2}$$

(2) Acoustic Velocity of Component (B)

The acoustic velocity of the component (B) was calculated by calculating a local elastic modulus of the component (B) with a scanning probe microscope (SPM-9700, manufactured by Shimadzu Corporation) by the JKR theory, and using the density of the component (B) by the following equation. The local elastic modulus was calculated by pushing a cantilever against the acoustic matching sheet to a depth of 5 nm. The density was determined in such a manner that a small amount of the component (B) was taken out from the acoustic matching sheet and analyzed as a sample with an analysis apparatus such as NNW, IR, or pyrolysis GC-MS to clarify the composition, and the density was determined based on this composition.

$$\text{Acoustic velocity} = (\text{local elastic modulus/density})^{1/2}$$

(3) Acoustic Velocity of Acoustic Matching Sheet (Acoustic Velocity (S) in Table 1 Which Will be Given Later)

With respect to the acoustic matching sheet produced above, the acoustic velocity at five portions (in each measurement portion, the entire inside of a circle with a diameter of 1.5 cm (small probe size of a single channel)) including the vicinity of the four corners and the central region of the sheet was measured at 25° C. using a sing-around acoustic velocity measurement apparatus (Model "UVM-2", trade name, manufactured by Ultrasonic Engineering Co., Ltd.) according to HS Z2353 (2003), and an arithmetic mean value of the measured values was taken as the acoustic velocity of the acoustic matching sheet. The obtained acoustic velocity was evaluated by applying it to the following evaluation standards. An evaluation of equal to or higher than "D" is acceptable in the present test.

—Evaluation Standards—

A: The acoustic velocity was reduced by 10% or more as compared with the corresponding acoustic matching sheet containing no resin particles.

B: The acoustic velocity was reduced by 7.5% or more and less than 10% as compared with the corresponding acoustic matching sheet containing no resin particles.

C: The acoustic velocity was reduced by 5% or more and less than 7.5% as compared with the corresponding acoustic matching sheet containing no resin particles.

D: The acoustic velocity was reduced by 2.5% or more and less than 5% as compared with the corresponding acoustic matching sheet containing no resin particles.

E: The acoustic velocity was the same or reduced by less than 2.5% as compared with the corresponding acoustic matching sheet containing no resin particles.

The "corresponding acoustic matching sheet containing no resin particles" is Comparative Example 4 for Examples 1 to 7 and 11 to 34 and Comparative Examples 1 to 3 and 6 to 11; Comparative Example 5 for Examples 8 to 10; Comparative Example 15 for Examples 35 to 41 and Comparative Examples 12 to 14; and Comparative Example 19 for Examples 42 to 48 and Comparative Examples 16 to 18, 20, and 21. The same applies to the following test examples.

<2> Measurement of Number Average Particle Diameter of Component (B)

The number average particle diameter of component (B) (resin particles) was calculated by observing an edge surface of the acoustic matching sheet with a scanning electron microscope (SU8030, trade name, manufactured by Hitachi High-Tech Corporation) in a visual field containing 100 or more particles, randomly extracting 100 particles from the component (B) in the visual field, and measuring the number average particle diameter of the extracted particles.

The acoustic matching sheet whose edge surface could not be observed by a scanning electron microscope was observed by ice-embedded transmission electron microscopy. Ice embedding was carried out by Vitrobot Mark IV (trade name, manufactured by FEI Company), and the number average particle diameter was calculated by randomly extracting 100 particles from the component (B) in the visual field with a transmission electron microscope (JEM-2010, trade name, manufactured by JEOL Ltd.) and measuring the number average particle diameter of the extracted particles.

In a case where the particles were not perfect circles, particles with a maximum ratio of vertical to horizontal diameter of 0.7 or more were extracted and measured, <3> Heat Resistance Test The heat resistance was evaluated from the glass transition temperature calculated by using a viscoelastometer (model name "DMS6100", manufactured by Seiko Instruments Inc.) for the viscoelasticity of the acoustic matching sheet. The measurement was carried out at 1 Hz, and the temperature at which tan δ became the maximum value was defined as the glass transition temperature. This glass transition temperature was evaluated by applying it to the following evaluation standards. An evaluation of equal to or higher than "C" is acceptable in the present test.

—Evaluation Standards—

A: The glass transition temperature was the same or lower by less than 5° C. as compared with the corresponding acoustic matching sheet containing no resin particles.

B: The glass transition temperature was lower by 5° C. or more and less than 7° C. as compared with the corresponding acoustic matching sheet containing no resin particles.

C: The glass transition temperature was lower by 7° C. or more and less than 9° C. as compared with the corresponding acoustic matching sheet containing no resin particles.

D: The glass transition temperature was lower by 9° C. or more and less than 10° C. as compared with the corresponding acoustic matching sheet containing no resin particles.

E: The glass transition temperature was lower by 10° C. or more as compared with the corresponding acoustic matching sheet containing no resin particles.

<4> Acoustic Wave (Ultrasonic Wave) Sensitivity Test

A sinusoidal signal (a wave) of 10 MHz which had been output from an ultrasound oscillator (function generator, trade name: "FG-350", manufactured by Iwatsu Electric Co., Ltd.) was input into an ultrasound probe (manufactured by JAPAN PROBE), and an ultrasound pulse wave with a center frequency of 10 MHz was generated in water from the ultrasound probe. The magnitude of the amplitude before and after the generated ultrasonic wave passed through each of the obtained acoustic matching sheet with a thickness of 2 mm was measured in a water temperature environment of 25° C. using an ultrasound receiver (oscilloscope, trade name: "VP-5204A", manufactured by Matsushita Electric Industrial Co., Ltd.).

The acoustic wave (ultrasonic wave) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained in a case where the ultrasound oscillator receives an acoustic wave (ultrasonic wave) that the acoustic wave (ultrasonic wave) generated passes through a sheet and is reflected from an opposite side of the sheet. The higher the acoustic wave (ultrasonic wave) sensitivity is, the smaller the acoustic wave (ultrasonic wave) attenuation is.

$$\text{Acoustic wave (ultrasonic wave) sensitivity} = 20 \times \text{Log}(Vs/Vin)$$

The acoustic wave (ultrasonic wave) sensitivity was evaluated according to the following evaluation standards. In the present test, the evaluation of higher than or equal to "C" is an acceptable level.

—Evaluation Standards—

A: There was no decrease in sensitivity as compared with the corresponding acoustic matching sheet containing no resin particles.

B: The decrease in sensitivity was less than 2.5% as compared with the corresponding acoustic matching sheet containing no resin particles.

C: The decrease in sensitivity was 2.5% or more and less than 5.0% as compared with the corresponding acoustic matching sheet containing no resin particles.

D: The decrease in sensitivity was 5.0% or more and less than 7.5% as compared with the corresponding acoustic matching sheet containing no resin particles.

E: The decrease in sensitivity was 7.5 or more as compared with the corresponding acoustic matching sheet containing no resin particles.

TABLE 1-A

| | Component (A1) | | Component (D) | | Component (B1) | | | Component (C) | | | | | |
|---|---|---|---|---|---|---|---|---|---|---|---|---|---|
| | Type | Parts by mass | Type | Parts by mass | Type | Particle diameter | Part(s) by mass | Type | Parts by mass | Specific gravity | Acoustic velocity (S) | Heat resistance | Sensitivity |
| Example 1 | A-1 | 11 | D-1 | 10 | PBd | 0.2 | 4 | Fe | 100 | 3.3 | A | A | A |
| Example 2 | A-1 | 12 | D-1 | 10 | PBd | 0.2 | 3 | Fe | 100 | 3.3 | A | A | A |
| Example 3 | A-1 | 13 | D-1 | 10 | PBd | 0.2 | 2 | Fe | 100 | 3.3 | A | A | A |
| Example 4 | A-1 | 14 | D-1 | 10 | PBd | 0.2 | 1 | Fe | 100 | 3.3 | B | A | A |
| Example 5 | A-1 | 11 | D-1 | 10 | PBd | 0.5 | 4 | Fe | 100 | 3.3 | A | A | B |
| Example 6 | A-1 | 11 | D-1 | 10 | PBd | 0.8 | 4 | Fe | 100 | 3.3 | A | A | C |
| Example 7 | A-1 | 11 | D-1 | 10 | PBd | 1.0 | 4 | Fe | 100 | 3.3 | A | A | C |
| Comparative Example 1 | A-1 | 11 | D-1 | 10 | PBd | 1.2 | 4 | Fe | 100 | 3.3 | A | A | D |
| Comparative Example 2 | A-1 | 11 | D-1 | 10 | PBd | 1.5 | 4 | Fe | 100 | 3.3 | A | A | E |
| Comparative Example 3 | A-1 | 11 | D-1 | 10 | PBd | 3.0 | 4 | Fe | 100 | 3.3 | A | A | E |
| Comparative Example 4 | A-1 | 15 | D-1 | 10 | — | — | — | Fe | 100 | 3.3 | E | A | A |
| Exutnple 8 | A-1 | 11 | D-1 | 10 | PBd | 0.2 | 4 | — | — | 1.4 | A | A | A |
| Example 9 | A-1 | 11 | D-1 | 10 | Silicone 1 | 0.2 | 4 | — | — | 1.3 | A | B | A |
| Example 10 | A-1 | 11 | D-1 | 10 | Acrylic resin particles 1 | 0.2 | 4 | — | — | 1.4 | B | B | A |
| Comparative Example 5 | A-1 | 15 | D-1 | 10 | — | — | — | — | — | 1.4 | E | A | A |
| Example 11 | A-1 | 11 | D-1 | 10 | PBd | 0.2 | 4 | Mo | 100 | 5.1 | A | A | A |
| Example 12 | A-1 | 11 | D-1 | 10 | PBd | 0.2 | 4 | WC | 100 | 6.0 | A | A | A |
| Example 13 | A-1 | 11 | D-1 | 10 | PBd | 0.2 | 4 | W | 100 | 6.3 | B | A | A |
| Example 14 | A-1 | 11 | D-1 | 10 | PIP | 0.2 | 4 | Fe | 100 | 3.3 | A | A | A |
| Example 15 | A-1 | 12 | D-1 | 10 | PIP | 0.2 | 3 | Fe | 100 | 3.3 | A | A | A |
| Example 16 | A-1 | 13 | D-1 | 10 | PIP | 0.2 | 2 | Fe | 100 | 3.3 | B | A | A |
| Example 17 | A-1 | 14 | D-1 | 10 | PIP | 0.2 | 1 | Fe | 100 | 3.3 | B | A | A |
| Example 18 | A-1 | 11 | D-1 | 10 | PIP | 0.5 | 4 | Fe | 100 | 3.3 | A | A | B |

TABLE 1-B

| | Component (A1) | | Component (D) | | Component (B1) | | | Component (C) | | | | | |
|---|---|---|---|---|---|---|---|---|---|---|---|---|---|
| | Type | Parts by mass | Type | Parts by mass | Type | Particle diameter | Part(s) by mass | Type | Parts by mass | Specific gravity | Acoustic velocity (S) | Heat resistance | Sensitivity |
| Example 19 | A-1 | 11 | D-1 | 10 | PIP | 0.8 | 4 | Fe | 100 | 3.3 | A | A | C |
| Example 20 | A-1 | 11 | D-1 | 10 | PIP | 1.0 | 4 | Fe | 100 | 3.3 | A | A | C |
| Example 21 | A-1 | 11 | D-1 | 10 | Silicone 1 | 0.2 | 4 | Fe | 100 | 3.3 | A | B | A |
| Example 22 | A-1 | 12 | D-1 | 10 | Silicone 1 | 0.2 | 3 | Fe | 100 | 3.3 | A | A | A |
| Example 23 | A-1 | 13 | D-1 | 10 | Silicone 1 | 0.2 | 2 | Fe | 100 | 3.3 | B | A | B |
| Example 24 | A-1 | 14 | D-1 | 10 | Silicone 1 | 0.2 | 1 | Fe | 100 | 3.3 | D | A | B |
| Comparative Example 6 | A-1 | 11 | D-1 | 10 | Silicone 2 | 2.0 | 4 | Fe | 100 | 3.3 | A | A | E |
| Comparative Example 7 | A-1 | 11 | D-1 | 10 | Silicone 3 | 3.0 | 4 | Fe | 100 | 3.3 | A | A | E |
| Example 25 | A-1 | 11 | D-1 | 10 | Acrylic resin particles 1 | 0.2 | 4 | Fe | 100 | 3.3 | B | B | A |
| Example 26 | A-1 | 11 | D-1 | 10 | Acrylic resin particles 1 | 0.2 | 3 | Fe | 100 | 3.3 | B | B | B |
| Example 27 | A-1 | 13 | D-1 | 10 | Acrylic resin particles 1 | 0.2 | 2 | Fe | 100 | 3.3 | B | B | B |
| Example 28 | A-1 | 14 | D-1 | 10 | Acrylic resin particles 1 | 0.2 | 1 | Fe | 100 | 3.3 | D | A | B |
| Comparative Example 8 | A-1 | 11 | D-1 | 10 | Acrylic resin particles 2 | 2.0 | 4 | Fe | 100 | 3.3 | B | A | E |
| Comparative Example 9 | A-1 | 11 | D-1 | 10 | Acrylic resin particles 3 | 4.0 | 4 | Fe | 100 | 3.3 | B | A | E |
| Comparative Example 10 | A-1 | 11 | D-1 | 10 | Liquid PBd | — | 4 | Fe | 100 | 3.3 | A | D | A |
| Comparative Example 11 | A-1 | 11 | D-1 | 10 | Silicone (non-particle) | — | 4 | Fe | 100 | 3.3 | A | E | A |
| Example 29 | A-2 | 11 | D-1 | 9 | PBd | 0.2 | 4 | Fe | 100 | 3.3 | A | A | A |
| Example 30 | A-3 | 11 | D-1 | 7 | PBd | 0.2 | 4 | Fe | 100 | 3.3 | A | A | A |
| Example 31 | A-4 | 11 | D-1 | 10 | PBd | 0.2 | 4 | Fe | 100 | 3.2 | A | A | A |
| Example 32 | A-5 | 11 | D-1 | 10 | PBd | 0.2 | 4 | Fe | 100 | 3.2 | A | A | A |

TABLE 1-B-continued

| | Component (A1) | | Component (D) | | Component (B1) | | | Component (C) | | | | | |
|---|---|---|---|---|---|---|---|---|---|---|---|---|---|
| | Type | Parts by mass | Type | Parts by mass | Type | Particle diameter | Part(s) by mass | Type | Parts by mass | Specific gravity | Acoustic velocity (S) | Heat resistance | Sensitivity |
| Example 33 | A-6 | 11 | D-1 | 7 | PBd | 0.2 | 4 | Fe | 100 | 3.3 | A | A | A |
| Example 34 | A-7 | 11 | D-1 | 12 | PBd | 0.2 | 4 | Fe | 100 | 3.3 | A | A | A |

TABLE 1-C

| | Component (A1) | | Component (D) | | Component (B1) | | | Component (C) | | | | | |
|---|---|---|---|---|---|---|---|---|---|---|---|---|---|
| | Type | Parts by mass | Type | Part(s) by mass | Type | Particle diameter | Part(s) by mass | Type | Parts by mass | Specific gravity | Acoustic velocity (S) | Heat resistance | Sensitivity |
| Example 35 | A-8 | | | 11 | PBd | 0.2 | 4 | Fe | 100 | 3.3 | A | A | A |
| Example 36 | A-8 | | | 11 | PBd | 0.2 | 3 | Fe | 100 | 3.3 | B | A | A |
| Example 37 | A-8 | | | 11 | PBd | 0.2 | 2 | Fe | 100 | 3.3 | C | A | A |
| Example 38 | A-8 | | | 11 | PBd | 0.2 | 1 | Fe | 100 | 3.3 | C | A | B |
| Example 39 | A-8 | | | 11 | PBd | 0.5 | 4 | Fe | 100 | 3.3 | A | A | B |
| Example 40 | A-8 | | | 11 | PBd | 0.8 | 4 | Fe | 100 | 3.3 | A | A | C |
| Example 41 | A-8 | | | 11 | PBd | 1.0 | 4 | Fe | 100 | 3.3 | A | A | C |
| Comparative Example 12 | A-8 | | | 11 | PBd | 1.2 | 4 | Fe | 100 | 3.3 | A | A | D |
| Comparative Example 13 | A-8 | | | 11 | PBd | 1.5 | 4 | Fe | 100 | 3.3 | A | A | E |
| Comparative Example 14 | A-8 | | | 11 | PBd | 3.0 | 4 | Fe | 100 | 3.3 | A | A | E |
| Comparative Example 15 | A-8 | | | 11 | — | — | — | Fe | 100 | 3.3 | E | A | A |
| Example 42 | A-9 | 11 | D-2 | 1 | PBd | 0.2 | 4 | Fe | 100 | 3.3 | B | A | A |
| Example 43 | A-9 | 12 | D-2 | 1 | PBd | 0.2 | 3 | Fe | 100 | 3.3 | C | A | B |
| Example 44 | A-9 | 13 | D-2 | 1 | PBd | 0.2 | 2 | Fe | 100 | 3.3 | C | A | B |
| Example 45 | A-9 | 14 | D-2 | 1 | PBd | 0.2 | 1 | Fe | 100 | 3.3 | D | A | B |
| Example 46 | A-9 | 11 | D-2 | 1 | PBd | 0.5 | 4 | Fe | 100 | 3.3 | B | A | B |
| Example 47 | A-9 | 11 | D-2 | 1 | PBd | 0.8 | 4 | Fe | 100 | 3.3 | B | A | C |
| Example 48 | A-9 | 11 | D-2 | 1 | PBd | 1.0 | 4 | Fe | 100 | 3.3 | B | A | C |
| Comparative Example 16 | A-9 | 11 | D-2 | 1 | PBd | 1.2 | 4 | Fe | 100 | 3.3 | B | A | E |
| Comparative Example 17 | A-9 | 11 | D-2 | 1 | PBd | 1.5 | 4 | Fe | 100 | 3.3 | B | A | E |
| Comparative Example 18 | A-9 | 11 | D-2 | 1 | PBd | 3.0 | 4 | Fe | 100 | 3.3 | B | A | E |
| Comparative Example 19 | A-9 | 15 | D-2 | 1 | — | — | — | Fe | 100 | 3.3 | E | A | A |
| Comparative Example 20 | A-9 | 11 | D-2 | 1 | Acrylic resin particles 1 | 0.2 | 4 | Fe | 100 | 3.3 | E | A | A |
| Comparative Example 21 | A-9 | 11 | D-2 | 1 | Acrylic resin particles 2 | 2.0 | 4 | Fe | 100 | 3.3 | E | A | E |

Examples 1 to 48, and Comparative Examples 1 to 3, 6 to 9, 12 to 14, and 16 to 18: it was confirmed by the scanning probe microscope (SPM) described above that the difference in acoustic velocity of "acoustic velocity of component (A)"—"acoustic velocity of component (B)" was 50 to 1500 m/s.

Comparative Examples 20 and 21: it was confirmed by SPM that the difference in acoustic velocity of "acoustic velocity of component (A)"—"acoustic velocity of component (B)" was −50 to −1500 m/s.

In a case where the component (B) can be made into a sheet having a length of 5 cm, a width of 5 cm, and a height of 2 mm in the same manner as in the above-mentioned production of the acoustic matching sheet, substantially the same results as in the above-mentioned method are obtained even in a case where a sheet consisting of the component (B) is produced, the acoustic velocity at five portions (in each measurement portion, the entire inside of a circle with a diameter of 1.5 cm (small probe size of a single channel)) including the vicinity of the four corners and the central region of the sheet is measured at 25° C. using a sing-around acoustic velocity measurement apparatus (Model "UVM-2", trade name, manufactured by Ultrasonic Engineering Co., Ltd.) according to HS 22353 (2003), and an arithmetic mean value of the measured values is taken as the acoustic velocity of the component (B).

Similarly, in a case where the component (A) can be made into a sheet of the above-mentioned size in the same manner as in the above-mentioned production of the acoustic matching sheet, substantially the same results as in the above-mentioned method are obtained even in a case where a sheet consisting of the component (A) is produced, the acoustic velocity at five portions including the vicinity of the four corners and the central region of the sheet is measured, and an arithmetic mean value of the measured values is taken as the acoustic velocity of the component (A).

That is, it can also be confirmed by these methods that the difference in acoustic velocity of "acoustic velocity of the component (A)"—"acoustic velocity of the component (B)" is within the above range.

The density of five measurement portions including the vicinity of the four corners and the central region of the sheet consisting of the component (A) or the sheet consisting of the component (B) is measured at 25° C. using an electronic hydrometer (trade name "SD-200L", manufactured by Alfa Mirage Co., Ltd.) according to the density measurement method of Method A (water displacement method) described in JIS K7112 (1999), and an arithmetic mean value of the measured values can also be adopted as the density of the component (A) or component (B). The density of the measurement portion is a density of a cut sheet piece (10 mm×10 mm square) obtained by cutting out a sheet piece into a square of 10 mm×10 mm in the acoustic velocity measurement portion (circle with a diameter of 1.5 cm).

<Notes of Tables>

[Component (A1)]

(A-1) bisphenol A diglycidyl ether ("jER825", trade name, manufactured by Mitsubishi Chemical Corporation, epoxy equivalent: 170)

(A-2) bisphenol A diglycidyl ether ("jER828", trade name, manufactured by Mitsubishi Chemical Corporation, epoxy equivalent: 190)

(A-3) bisphenol A diglycidyl ether ("jER834", trade name, manufactured by Mitsubishi Chemical Corporation, epoxy equivalent: 230)

(A-4) bisphenol F diglycidyl ether ("EPICLON 830", trade name, manufactured by DIC Corporation, epoxy equivalent: 170)

(A-5) epoxy novolac resin (product number 406775, manufactured by Sigma-Aldrich Co. LLC, epoxy equivalent: 170)

(A-6) bisphenol A propoxylate diglycidyl ether (manufactured by Sigma-Aldrich Co. LLC, epoxy equivalent: 228)

(A-7) 4,4'-methylenebis(N,N-diglycidylaniline) (manufactured by Tokyo Chemical Industry Co., Ltd., epoxy equivalent: 106)

(A-8) nylon 12 (manufactured by Kureha Extron Co., Ltd.)

(A-9) polyisoprene rubber ("Nipol IR2200", trade name, manufactured by Zeon Corporation)

[Component (B1)]

PBd: polybutadiene rubber particles (particles prepared according to the following method)

200 parts by mass of ultrapure water, 0.03 parts by mass of tripotassium phosphate, 0.002 parts by mass of disodium ethylenediamine tetraacetate, 0.001 parts by mass of ferrous sulfate heptahydrate, and 1.55 parts by mass of sodium dodecyl sulfate were added to a pressurized container which was then purged with nitrogen. Then, 100 parts by mass of butadiene were added, followed by heating to 45° C. 0.03 parts by mass of para-menthane hydroperoxide and then 0.10 parts by mass of SFS were added to initiate polymerization. 0.025 parts by mass of para-menthane hydroperoxide were additionally added 3 hours, 5 hours, and 7 hours after the start of the polymerization. In addition, 0.0006 parts by mass of disodium ethylenediamine tetraacetate and 0.003 parts by mass of ferrous sulfate heptahydrate were additionally added 4, 6, and 8 hours after the start of the polymerization. After 15 hours from the start of the polymerization, the pressure was reduced to remove the residual monomer to complete the polymerization, and polybutadiene rubber particles containing polybutadiene rubber as a main component were obtained. The number average particle diameter of the obtained polybutadiene rubber particles was 0.1 µm.

By repeating the above polymerization using the obtained rubber particles as seed particles, each polybutadiene rubber particle having a number average particle diameter shown in Table 1 was obtained.

Silicone 1: silicone particles (particles prepared by crushing TOSPEARL XC99-A8808, trade name, manufactured by Momentive Performance Materials Japan LLC)

Silicone 2: silicone particles (TOSPEARL 120A, trade name, manufactured by Momentive Performance Materials Japan LLC)

Silicone 3: silicone particles (TOSPEARL 130, trade name, manufactured by Momentive Performance Materials Japan LLC)

Acrylic resin particles 1: acrylic resin particles (particles prepared by crushing EPOSTAR MA1002, trade name, manufactured by Nippon Shokubai Co., Ltd.)

Acrylic resin particles 2: acrylic resin particles (EPOSTAR MA1002, trade name, manufactured by Nippon Shokubai Co., Ltd.)

Acrylic resin particles 3: acrylic resin particles (EPOSTAR MA1004, trade name, manufactured by Nippon Shokubai Co., Ltd.)

PIP: polyisoprene rubber particles (particles prepared according to the following method)

Sodium dodecyl sulfate (5.60 g), ultrapure water (86.50 g), t-butyl hydroperoxide (0.035 g), and t-dodecyl mercaptan (0.0053 g) were added to a glass reaction container (200 mL) equipped with a cooling pipe and a mechanical stirrer. The container was purged with argon gas at 25° C. for 1 hour. Then, isoprene (3.6 g) and tetraethylenepentamine (0.033 g) were added and reacted for 24 hours with stirring at 450 rpm. After 24 hours from the start of the polymerization, the pressure was reduced to remove the residual monomer to complete the polymerization, and polyisoprene rubber particles containing polyisoprene rubber as a main component were obtained. The number average particle diameter of the polyisoprene rubber particles contained in the obtained latex was 0.2 µm.

By repeating the above polymerization using the obtained rubber particles as seed particles, each polyisoprene rubber particle having a number average particle diameter shown in Table 1 was obtained.

Liquid PBd: liquid polybutadiene (B-1000, trade name, manufactured by Nippon Soda Co., Ltd.)

Silicone (non-particle) (X-22-163, trade name, manufactured by Shin-Etsu Silicone Co., Ltd.)

In Comparative Examples 10 and 11, liquid PBd and Silicone (non-particles) are listed in the column of component (B1) for comparison with Examples.

[Component (C)]

Fe: iron powder (EW-I, trade name, manufactured by BASF SE, average particle diameter: 2 µm)

Mo: molybdenum powder (Mo-3, trade name, manufactured by Japan New Metals Co., Ltd., average particle diameter: 3 µm)

WC: tungsten carbide powder (WC30S, manufactured by A.L.M.T. Corp., average particle diameter: 3 µm)

W: tungsten powder (W-U030, manufactured by A.L.M.T. Corp., average particle diameter: 3 µm)

[Component (D)]

(D-1) curing agent represented by the chemical formula hereinbefore (D-2) dicumyl peroxide (PERCUMYL D-40, trade name, manufactured by NOF Corporation)

The "particle diameter" refers to a number average particle diameter.

Examples 35 to 41 and Comparative Examples 12 to 15 do not use the component (D). The component (A1) and the amount thereof used are described.

The "-" means that the corresponding component is not used.

As is clear from Table 1, the sheets of Comparative Examples 1 to 3, 6, 7, 8, 9, 12 to 14, 16 to 18, and 21 using particles having a number average particle diameter of more than 1.0 µm were at least insufficient in acoustic wave sensitivity. In addition, the sheets of Comparative Examples 4, 5, 15, and 19 containing no component (B) had a high acoustic velocity. In addition, the sheet of Comparative Example 10 using liquid polybutadiene rubber and the sheet of Comparative Example 11 using non-particle silicone had an insufficient heat resistance. In addition, in the sheet of Comparative Example 20, the acoustic velocity of the component (B) was higher than that of the component (A), and the acoustic velocity of the sheet was also higher.

On the other hand, the sheet of the present invention was acceptable in all the evaluation items.

The present invention has been described with reference to embodiments thereof. However, it is considered that, unless otherwise specified, even the detailed description of the invention is not limited and is necessarily widely interpreted without departing from the gist and the range of the invention shown in the attached Claims.

EXPLANATION OF REFERENCES

1: acoustic lens
2: acoustic matching layer
3: piezoelectric element layer
4: backing material
7: housing
9: cord
10: ultrasound probe

What is claimed is:

1. An acoustic matching sheet comprising the following component (B) in the following component (A):
   (A): at least one of a resin or a rubber, and
   (B): at least one of a resin particle or a rubber particle having an acoustic velocity lower than an acoustic velocity of the component (A) and having a number average particle diameter of 1.0 µm or less.

2. The acoustic matching sheet according to claim 1, wherein the number average particle diameter of the component (B) is 0.5 µm or less.

3. The acoustic matching sheet according to claim 2, wherein the number average particle diameter of the component (B) is 0.2 µm or less.

4. The acoustic matching sheet according to claim 1, wherein the component (A) is at least one of an epoxy resin or a polyamide resin.

5. The acoustic matching sheet according to claim 4, wherein the component (A) is an epoxy resin.

6. The acoustic matching sheet according to claim 5, wherein the component (A) is at least one of a bisphenol A type epoxy resin, a bisphenol F type epoxy resin, or a phenol novolac type epoxy resin.

7. The acoustic matching sheet according to claim 1, wherein the component (B) is at least one of an acrylic resin particle, a silicone resin particle, or a rubber particle.

8. The acoustic matching sheet according to claim 7, wherein the component (B) is at least one of a silicone resin particle or a rubber particle.

9. The acoustic matching sheet according to claim 8, wherein the component (B) is a rubber particle.

10. The acoustic matching sheet according to claim 1, further comprising (C): a metal particle.

11. The acoustic matching sheet according to claim 10, wherein a metal element constituting the component (C) includes at least one of metal elements of Groups 4 to 13.

12. The acoustic matching sheet according to claim 11, wherein the metal element constituting the component (C) includes at least one of Zn, In, Au, Ag, Co, Zr, W, Ta, Fe, Cu, Ni, Nb, Pt, Mn, or Mo.

13. A composition for an acoustic matching layer, comprising components (A1) and (B1):
   (A1): at least one of a resin or a rubber, and
   (B1): at least one of a resin particle or a rubber particle having an acoustic velocity lower than an acoustic velocity of the component (A1) and having a number average particle diameter of 1.0 µm or less.

14. An acoustic wave probe comprising the acoustic matching sheet according to claim 1 in an acoustic matching layer.

15. An acoustic wave measurement apparatus comprising the acoustic wave probe according to claim 14.

16. The acoustic wave measurement apparatus according to claim 15, wherein the acoustic wave measurement apparatus is an ultrasound diagnostic apparatus.

17. A method for manufacturing an acoustic wave probe, comprising a step of forming an acoustic matching layer using the composition for an acoustic matching layer according to claim 13.

* * * * *